(12) United States Patent
Hatta et al.

(10) Patent No.: US 9,775,967 B2
(45) Date of Patent: Oct. 3, 2017

(54) ELONGATED MEMBER

(71) Applicant: TERUMO KABUSHIKI KAISHA, Tokyo (JP)

(72) Inventors: Tomonori Hatta, Kanagawa (JP); Yuichi Tada, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/873,626

(22) Filed: Oct. 2, 2015

(65) Prior Publication Data

US 2016/0022960 A1 Jan. 28, 2016

Related U.S. Application Data

(63) Continuation of application No. PCT/JP2013/060545, filed on Apr. 5, 2013.

(51) Int. Cl.
*A61M 25/01* (2006.01)
*A61B 1/005* (2006.01)
*A61B 17/00* (2006.01)

(52) U.S. Cl.
CPC ....... *A61M 25/0147* (2013.01); *A61B 1/0055* (2013.01); *A61B 17/00234* (2013.01);
(Continued)

(58) Field of Classification Search
CPC ............ A61B 17/00234; A61B 1/0055; A61B 2017/00309; A61B 2017/00314;
(Continued)

(56) References Cited

U.S. PATENT DOCUMENTS 2,515,366 A * 7/1950 Zublin ............... E21B 7/06
138/120
5,807,241 A 9/1998 Heimberger
(Continued)

FOREIGN PATENT DOCUMENTS

JP H09117413 A 5/1997
JP 2009511107 A 3/2009
(Continued)

OTHER PUBLICATIONS

English Abstract of JP2009142389A, listed above under Foreign Patend Documents; 1 page.
(Continued)

*Primary Examiner* — Bhisma Mehta
*Assistant Examiner* — Brandy S Lee

(57) ABSTRACT

An elongated member which is deflectable and hollow and which is configured for deflection that follows the shape of a biological organ for smooth movement within the organ. The elongated member includes: an operating member configured to deflect the elongated member or deform the elongated member into a linear state; and a deflection mechanism at least including a guide portion having a grooved portion formed thereon, an engaging portion engageable with the grooved portion and a supporting portion configured to support the engaging portion for relative movement on the guide portion; a gap being formed between the guide portion and the engaging portion so as to allow movement of the engaging portion in the grooved portion.

17 Claims, 15 Drawing Sheets

(52) U.S. Cl.
CPC .................. *A61M 25/0138* (2013.01); *A61B 2017/00309* (2013.01); *A61B 2017/00314* (2013.01); *A61B 2017/00318* (2013.01)

(58) Field of Classification Search
CPC ...... A61B 2017/00318; A61B 17/1631; A61B 2017/320032; A61B 17/32002; A61B 17/3207; A61B 17/320758; A61B 2017/00292; A61B 2017/003; A61B 2017/2905; A61M 25/0138; A61M 25/0147; E21B 17/20; F16C 1/04
See application file for complete search history.

(56) References Cited

U.S. PATENT DOCUMENTS

| | | | | |
|---|---|---|---|---|
| 5,857,964 A * | 1/1999 | Konstorum | .......... | A61B 1/0055 600/139 |
| 2006/0167416 A1* | 7/2006 | Mathis | ............... | A61B 10/0275 604/164.01 |
| 2008/0243106 A1* | 10/2008 | Coe | .................. | A61B 17/00234 606/1 |
| 2010/0151161 A1* | 6/2010 | Da Rolo | ............ | A61B 17/1631 428/34.1 |
| 2012/0143175 A1* | 6/2012 | Hermann | ........... | A61B 17/1631 606/1 |

FOREIGN PATENT DOCUMENTS

| | | |
|---|---|---|
| JP | 2009142389 A | 7/2009 |
| JP | 2011067423 A | 4/2011 |
| JP | 2012183190 A | 9/2012 |
| JP | 2012527918 A | 11/2012 |
| JP | 2012528651 A | 11/2012 |
| WO | 2010140083 A2 | 12/2010 |

OTHER PUBLICATIONS

English Abstract of JP2011067423A, listed above under Foreign Patend Documents; 1 page.
English Abstract of JP20121813190A, listed above under Foreign Patend Documents; 1 page.

* cited by examiner

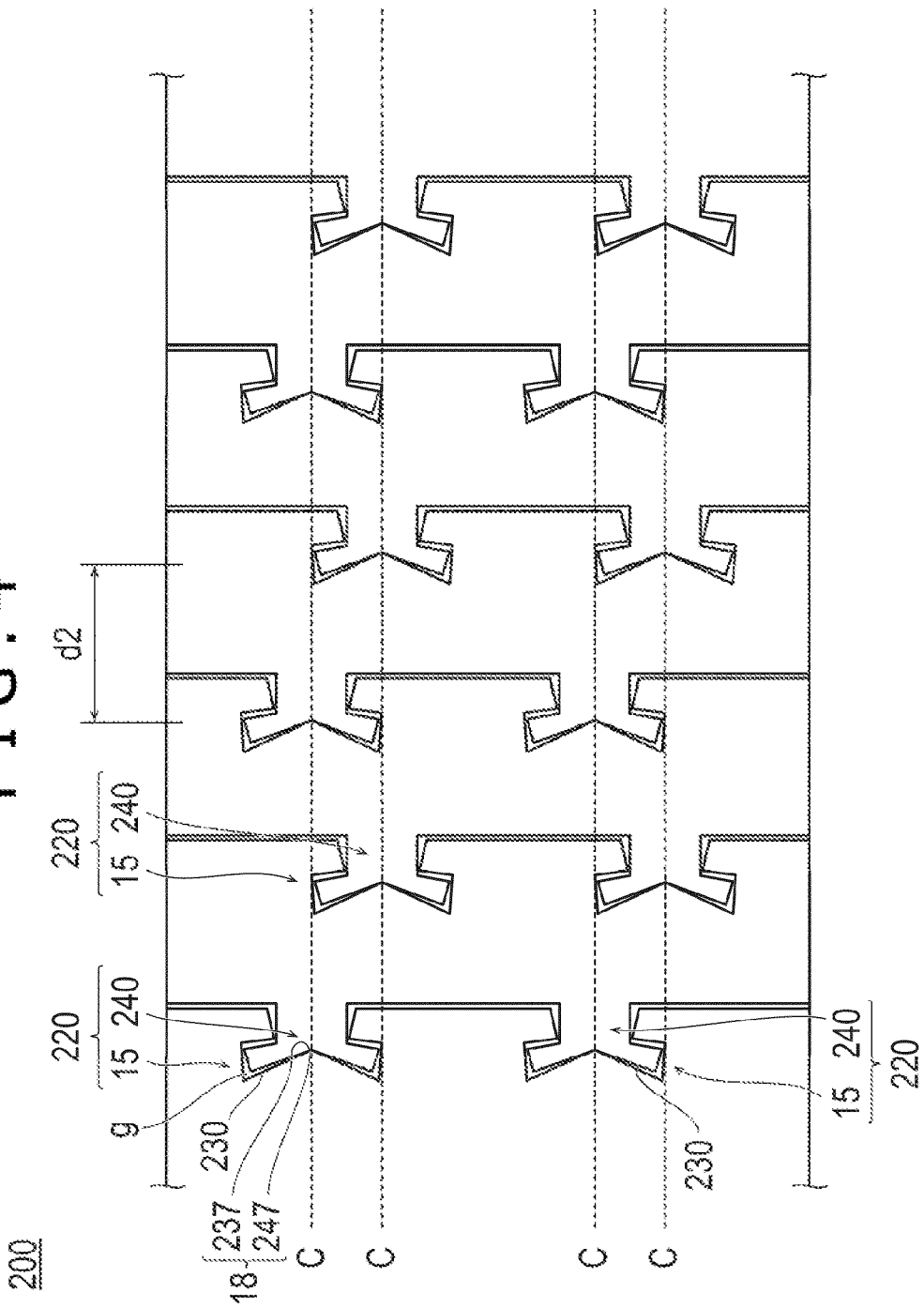

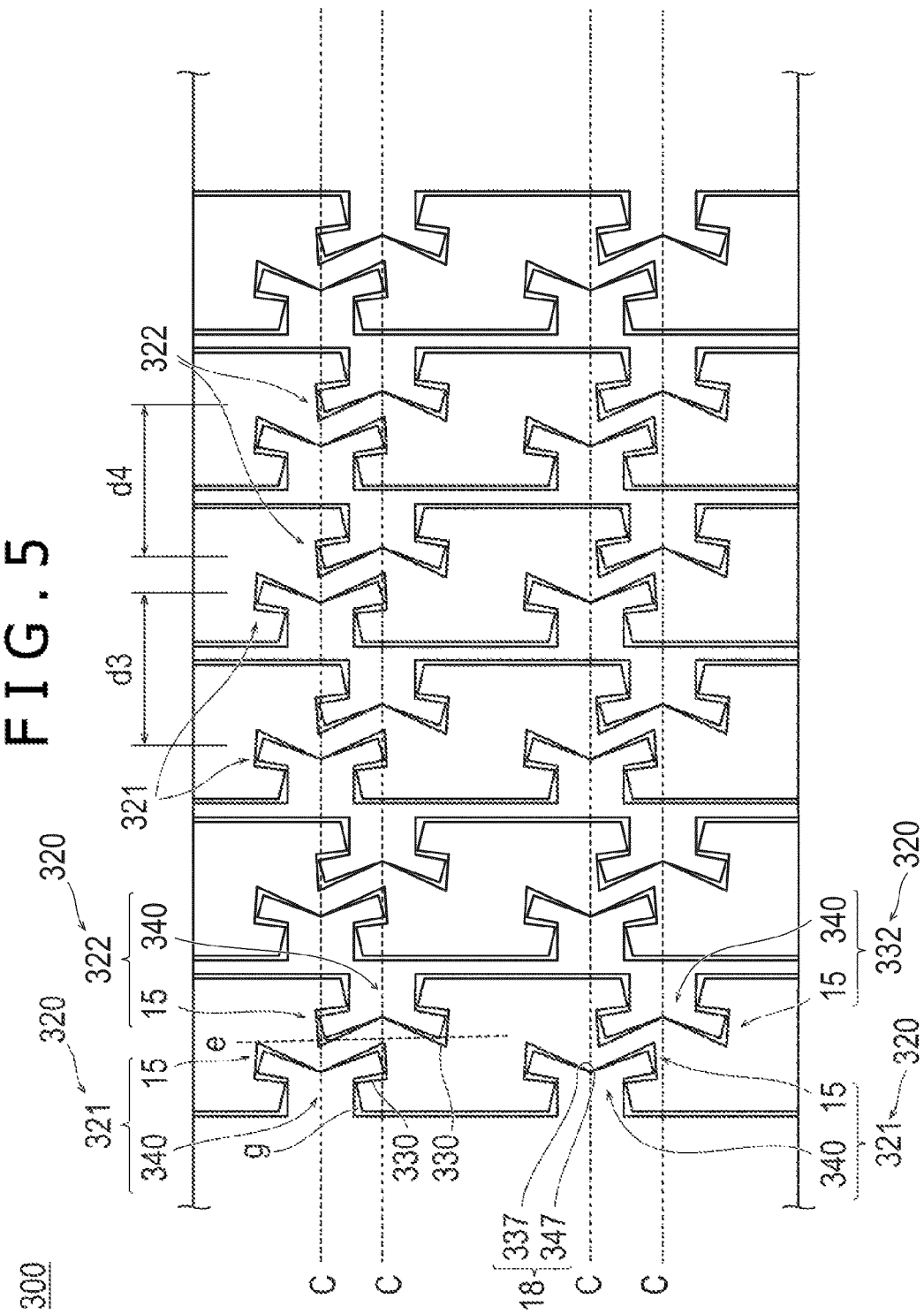

P2

ELONGATED MEMBER

CROSS REFERENCE TO RELATED APPLICATIONS

This application is a continuation International Application No. PCT/JP2013/060545, with an international filing date of Apr. 5, 2013. The entire contents of which are incorporated herein by reference.

BACKGROUND

The present disclosure relates to a hollow elongated member configured for deflection.

A hollow elongated member is used as an access tool for introducing various medical devices into a body cavity or a lumen of a living body or as a member which configures an insertion portion or the like of a flexible endoscope. An elongated member of the type described is configured such that it can deflect following a shape or the like of a biological organ so that a movement thereof in the living body can be carried out smoothly.

Japanese Patent Laid-Open No. Hei 9-117413) discloses an elongated member as a member for use for an insertion portion of a flexible endoscope. The elongated member is configured by connecting a plurality of first tubular elements having a groove formed thereon and a plurality of second tubular elements having a projected engaging portion provided thereon for engaging with the groove. In the elongated member, a push-pull member connected to the elongated member or the like is pulled by a hand to move adjacent ones of the tubular elements relative to each other to deflect the elongated member. Further, an operation for loosening the force applied by the pulling is carried out to deform the elongated member into a linear shape.

In such an elongated member as described above, the force applied to deflect the elongated member is transmitted from the proximal end side to the distal end side through engagement between the groove and the engaging portion of the tubular elements. Therefore, the ease in transmission of force upon operation depends much upon the shape of the groove, engaging portion and and other relevant features of the tubular elements.

SUMMARY OF THE DISCLOSURE

As an example, where a gap is formed in a shape substantially same as an outer shape of the engaging portion, the movement (pivotal movement) of the engaging portion in the groove is restricted as disclosed in Japanese Patent Laid-Open No. Hei 9-117413. Therefore, a rotational moment generated when the engaging portion moves is not transmitted efficiently along a longitudinal direction of the elongated member. Therefore, the deflection motion of the elongated member does not follow the operation of the push-pull member and the deflection motion is not carried out smoothly. Further, since the range of the movement of the engaging portion is limited, the deflection amount is also limited, and deflection of the elongated member following the shape of a biological organ or the like is not readily carried out. Accordingly, where the elongated member described above is used as a component of a medical device or the like, it degrades the operability of the medical device and hence degrades the usability of the medical device.

It is an intention of the present disclosure to provide an elongated member in which a movement of an engaging portion in a grooved portion provided on a deflection mechanism can be transmitted favorably from the proximal end side to the distal end side thereby to allow a deflection motion to be carried out smoothly and which can be deformed suitably following a shape of a biological organ or the like.

In order to attain the intention described above, according to the present disclosure, there is provided an elongated member which is deflectable and hollow. The elongated member including: an operating member configured to deflect the elongated member or deform the elongated member into a linear state; and a deflection mechanism at least including a guide portion having a grooved portion formed thereon, an engaging portion engageable with the grooved portion and a supporting portion configured to support the engaging portion for relative movement on the guide portion; a gap being formed between the guide portion and the engaging portion so as to allow movement of the engaging portion in the grooved portion.

With the elongated member, if predetermined force is applied to the elongated member through the operating member in order to carry out a deflection motion, then the engaging portion moves with respect to the guide portion provided on the deflection mechanism around a fulcrum provided by the supporting portion. Then, the movement is transmitted in the longitudinal direction of the elongated member. Therefore, the deflection motion of the elongated member can be carried out smoothly. Further, since the range within which the engaging portion can move can be expanded by the gap formed between the guide portion and the engaging portion, deformation of the elongated member can be carried out following a shape of a biological organ or the like.

Preferably, the guide portion, at least, has a first guide face formed so as to extend in a direction crossing with an axial line along a longitudinal direction of the elongated member; a second guide face formed in a symmetrical manner with the first guide face with respect to an axis of symmetry provided by the axial line; a third guide face formed at a position opposing to the first guide face, and a fourth guide face formed at a position opposing to the second guide face; the engaging portion at least has first to fourth abutting portions disposed at positions opposing to the first to fourth guide faces, respectively. The engaging portion is held for movement by the gap to a first position at which the first abutting portion abuts with the first guide face and the fourth abutting portion abuts with the fourth guide face and to a second position at which the second abutting portion abuts with the second guide face and the third abutting portion abuts with the third guide face.

With the elongated member, the engaging portion moves to the first position and the second position within the grooved portion provided on the deflection mechanism. Upon such movement, the first and fourth guide faces of the guide portion and the first and fourth abutting portions of the engaging portion abut with each other, respectively, or the second and third guide faces of the guide portion and the second and third abutting portions of the engaging portion abut with each other, respectively, whereupon force is transmitted in the longitudinal direction of the elongated member. Since force can be transmitted efficiently in the longitudinal direction of the elongated member through the abutment between the guide faces and the abutting portions, the deflection motion of the elongated member can be carried out smoothly.

In this instance, the deflection mechanism preferably has a face shape formed such that the first and second guide faces are formed in an inclined relationship along a circumferential direction with respect to the axial line and the first and second abutting portions abut at least at part thereof with the first and second guide faces, respectively.

With the elongated member, since the first and second abutting portions contact in plane with the first and second guide faces of the guide portion provided on the deflection mechanism, force applied to the elongated member can be transmitted in a higher efficiency in the longitudinal direction. Further, since the deflection shape is maintained in the state in which the guide faces and the abutting portions contact with each other in plane, the deflection shape of the elongated member can be maintained suitably. Consequently, occurrence of an inadvertent change in shape of the elongated member upon deflection motion can be prevented with certainty.

The elongated member preferably has a deflection region formed such that a plurality of deflection mechanisms are disposed at different positions from each other in the longitudinal direction of the elongated member in the deflection region; and the deflection region has a first deflection region, and a second deflection region which is formed on the proximal end side of the elongated member with respect to the first deflection region and in which a spacing distance between the deflection mechanisms neighboring with each other in the longitudinal direction is greater than a spacing distance between the deflection mechanisms neighboring with each other in the longitudinal direction in the first deflection region.

With the elongated member, the spacing distance between the deflection mechanisms neighboring with each other in the longitudinal direction in the second deflection region is set greater than the spacing distance between the deflection mechanisms neighboring with each other in the longitudinal direction in the first deflection region. Therefore, the elongated member can carry out a deflection motion with curvatures different from each other at a plurality of different locations thereof in the longitudinal direction. Accordingly, various models of elongated members conforming to product specifications for medical tools and so forth can be provided.

In this case, preferably the deflection region has a different deflection region in which the grooved portions of at least a set of ones of the deflection mechanisms which neighbor with each other in the longitudinal direction of the elongated member are opposed to each other.

With the elongated member, the grooved portions of at least one set of the deflection mechanisms neighboring with each other are disposed in an opposing relationship to each other in the different deflection region formed on the elongated member. Therefore, when the different deflection region is to be deflected, the deflection motion can be started smoothly with lower force.

In this case, at least one set of the deflection mechanisms which neighbor with each other in the longitudinal direction of the elongated member is disposed in such a manner that the deflection mechanisms are positioned at positions different from each other in a circumferential direction of the elongated member.

With the elongated member, since at least one set of the deflection mechanisms which neighbor with each other in the longitudinal direction of the elongated member is disposed in such a manner that they are positioned at positions different from each other in the circumferential direction of the elongated member, it is possible to permit movement of the engaging portions at a plurality of locations in the circumferential direction, and the elongated member can be deflected more readily.

A plurality of guide portions and a plurality of engaging portions are preferably formed at positions different from each other in a circumferential direction of the elongated member; and the grooved portions of the guide portions formed at positions different from each other in the circumferential direction are communicated with each other through a side groove extending in the circumferential direction.

With the elongated member, since the plurality of guide portions and the plurality of engaging portions are formed at the positions different from each other in the circumferential direction of the elongated member and the grooved portions are communicated with each other through the side groove extending in the circumferential direction of the elongated member, the range within which the portions of the elongated member move in the circumferential direction can be expanded. Further, the deflection motion can be carried out smoothly with lower force.

The operating member is preferably configured from a push-pull member configured to be subject to a pushing or pulling operation in the longitudinal direction of the elongated member to deflect the elongated member or deform the elongated member into the linear state.

With the elongated member, it is possible to deflect the elongated member or deform the elongated member into the linear state by a simple operation of pushing or pulling the push-pull member, which configures the operating member, along the longitudinal direction of the elongated member. Therefore, the elongated member is improved in convenience in use.

In this case, the operating member is disposed in a threading groove formed so as to extend in the longitudinal direction of the elongated member.

With the elongated member, since the operating member is disposed in the threading groove formed on the elongated member, the elongated member can be configured with a reduced diameter regardless of the installation of the operating member.

In this case, preferably the elongated member further includes an elastic member configured to cover an outer surface of the operating member disposed in the threading groove and the elongated member.

With the elongated member, since the elastic member which covers the outer surface of the elongated member is provided, circulation of fluid to the inner side and the outer side of the elongated member through the grooved portion can be prevented. Further, it is possible to achieve protection of the elongated member and protection of a living body of an introduction target. In addition, elasticity can be provided to the elongated member such that the elongated member can be configured so as to be elastically deformable and occurrence of coming off of the operating member from the threading groove can be prevented favorably.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

FIG. 4 is a developed view depicting the elongated member developed in a broken line region 4 in FIG. 1;

FIG. 5 is a developed view depicting the elongated member developed in a broken line region 5 in FIG. 1;

DETAILED DESCRIPTION OF THE PREFERRED EMBODIMENTS

An embodiment of the present disclosure is now described with reference to the drawings. It is to be noted that a dimensional rate in the figures is exaggerated for the convenience of illustration and is sometimes different from an actual ratio.

Figure 1:
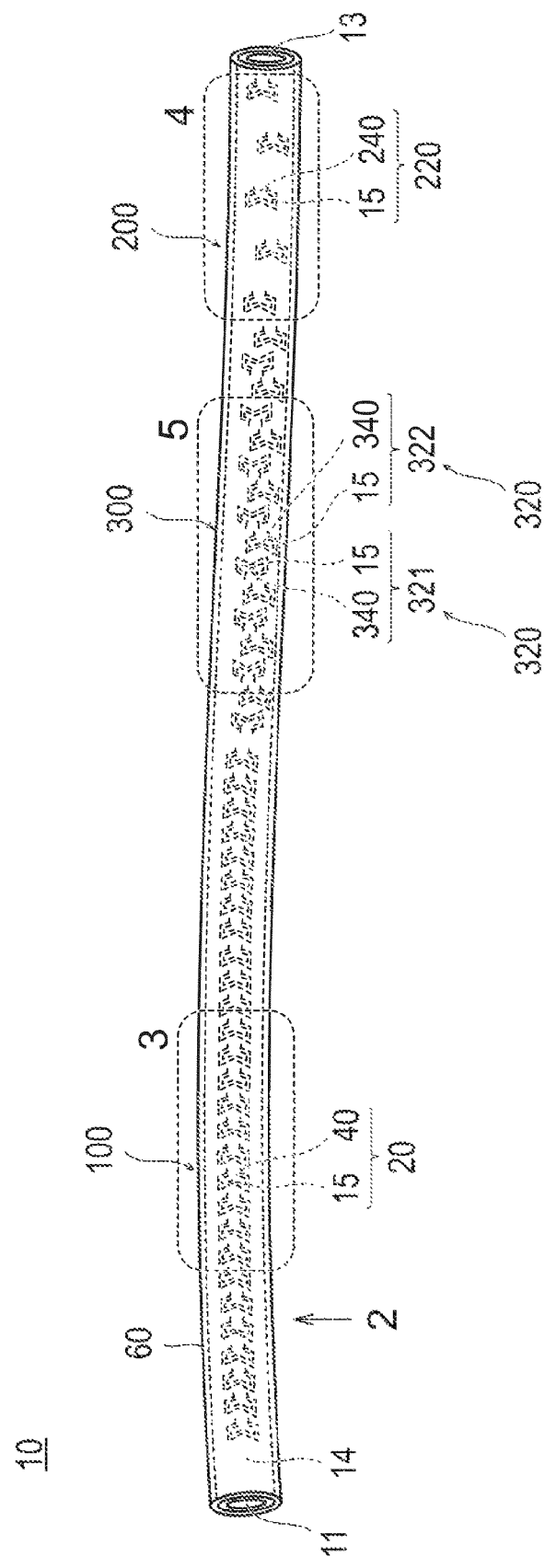
FIG. 1 is a schematic view depicting an elongated member according to an embodiment of the present disclosure in a simplified form.

FIGS. 1 to 5 depict a configuration of components of an elongated member according to one embodiment, and FIGS. 6A to 8C illustrate different actions of the elongated member of the embodiment. It is to be noted that, in the following description, the left side of the elongated member in FIG. 1 is referred to as "distal end side of the elongated member" and the right side is referred to as "proximal end side of the elongated member." Further, the leftward and rightward direction of the elongated member in FIG. 1 is referred to as "longitudinal direction of the elongated member."

Referring first to FIG. 1, an elongated member 10 according to the present embodiment is configured as a deflectable hollow elongated member and has an outer shape elongated in the longitudinal direction. As hereinafter described, if a predetermined operation is performed for the elongated member 10, then a deflection motion in which at least part of the elongated member 10 is deflected is carried out. The elongated member 10 can be used in various devices, tools, instruments and the like, used in the medical field, and can be used, for example, as a guiding tool for introducing a medical tool, instrument or the like to a predetermined target region in a living body through a body cavity or a lumen (for example, a blood vessel, the bile duct, a respiratory tract, a digestive tract, the urethra and so forth) of the living body, through an insertion portion of a flexible endoscope, or through a member configuring a shaft portion of a balloon catheter or the like.

The components of the elongated member according to the present embodiment are described in detail below.

Figure 2:
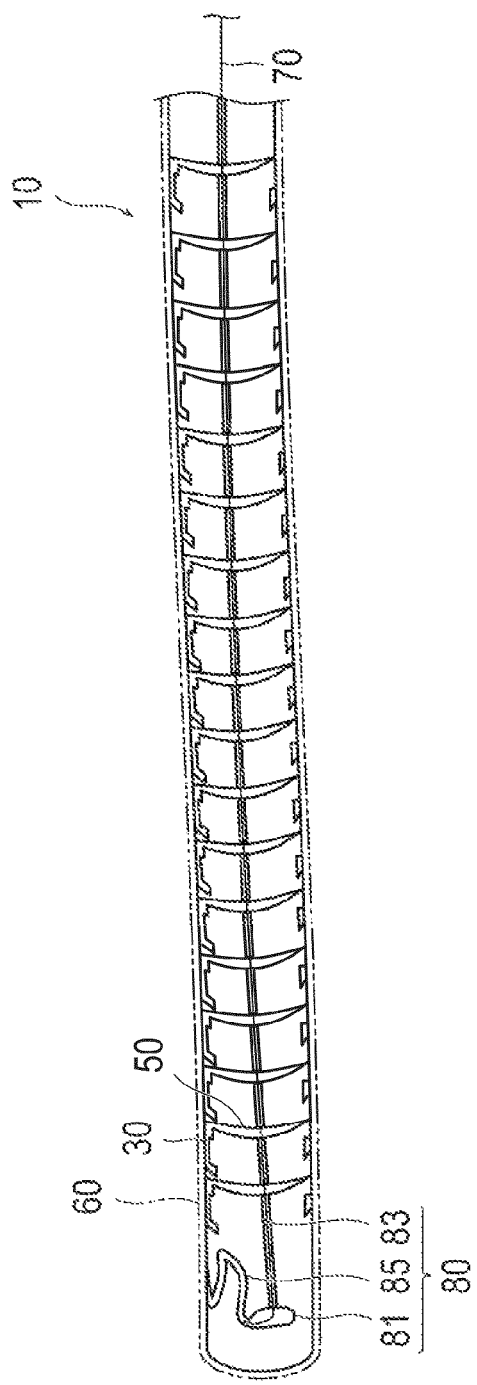
FIG. 2 is a partial enlarged view depicting a distal end portion of the elongated member as viewed in a direction indicated by an arrow mark 2 in FIG. 1.
Figure 3:
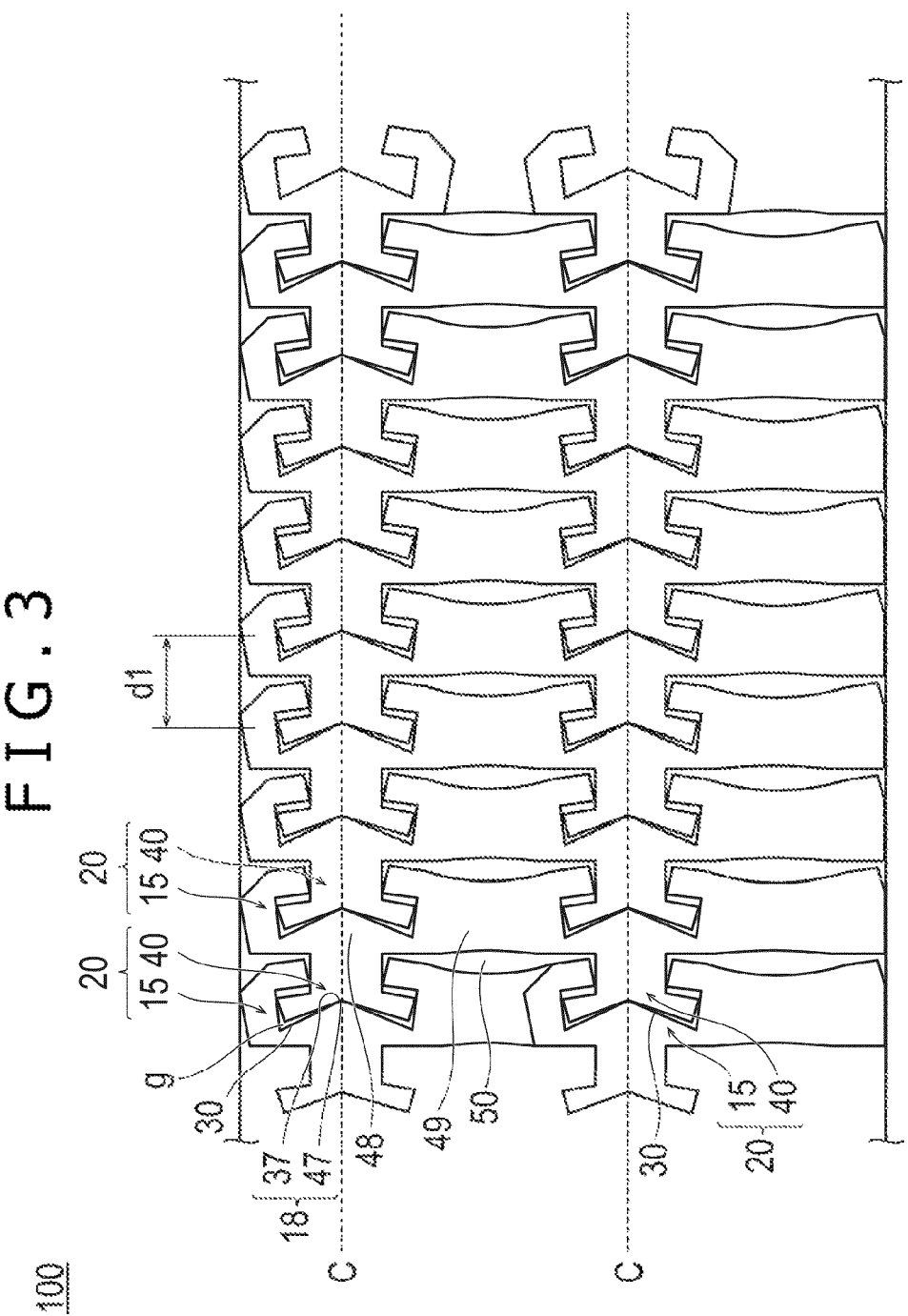
FIG. 3 is a developed view depicting the elongated member developed in a broken line region 3 in FIG. 1.

As depicted in FIGS. 1, 2 and 3, the elongated member 10 includes an operating member 70 (FIG. 2) for deflecting the elongated member 10 or deforming the elongated member 10 to a linear state, and a deflection mechanism 20. The deflection mechanism 20 at least includes a guide portion 15 having a grooved portion 30 formed thereon, an engaging portion 40 engageable with the grooved portion 30, and a supporting portion 18 for supporting the engaging portion 40 for relative movement on the guide portion 15. A gap g is formed between the guide portion 15 and the engaging portion 40 such that it permits a movement of the engaging portion 40 in the grooved portion 30.

Figure 6A:
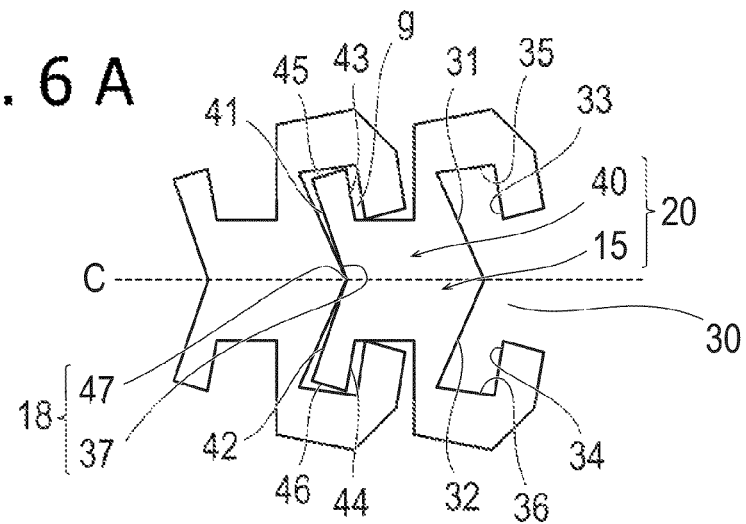
FIG. 6A is a plan view depicting, in an enlarged scale, a guide portion and an engaging portion provided in a first deflection region and illustrating an action of the elongated member depicted in FIG. 1.

As depicted in FIGS. 3 and 6A, the guide portion 15 at least has a first guide face 31, a second guide face 32, a third guide face 33 and a fourth guide face 34. The first guide face 31 is formed so as to extend in a direction crossing with an axial line C extending along the longitudinal direction of the elongated member 10. The second guide face 32 is formed symmetrically with the first guide face 31 with respect to an axis of symmetry provided by the axial line C. The third guide face 33 is formed at a position opposing to the first guide face 31, and the fourth guide face 34 is formed at a position opposing to the second guide face 32. Further, the engaging portion 40 includes a first abutting portion 41, a second abutting portion 42, a third abutting portion 43 and a fourth abutting portion 44. The first abutting portion 41 is disposed at a position opposing to the first guide face 31. The second abutting portion 42 is disposed at a position opposing to the second guide face 32. The third abutting portion 43 is disposed at a position opposing to the third guide face 33, and the fourth abutting portion 44 is disposed at a position opposing to the fourth guide portion 34.

Figure 6B:
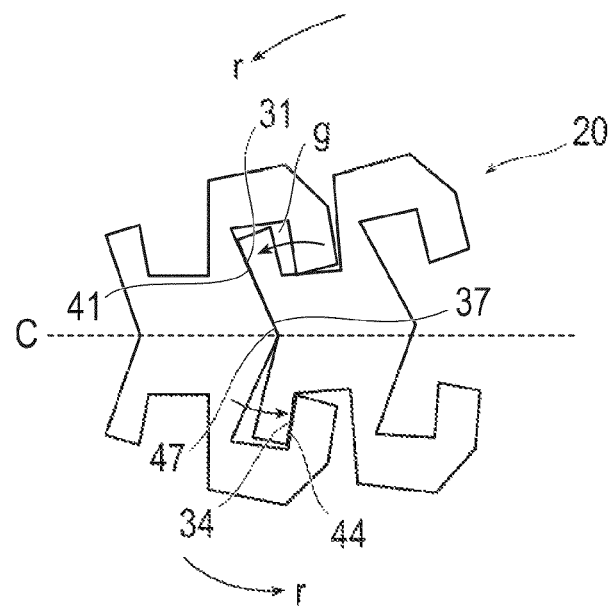
FIG. 6B is a plan view depicting, in an enlarged scale, a manner in which the engaging portion provided in the first deflection region moves and illustrating an action of the elongated member depicted in FIG. 1.
Figure 6C:
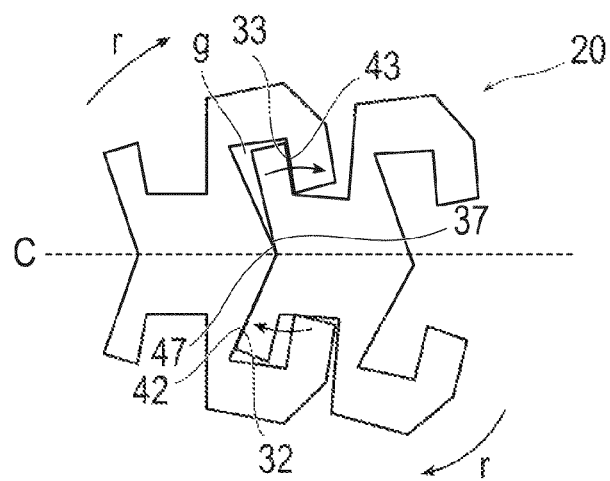
FIG. 6C is a plan view depicting, in an enlarged scale, another manner in which the engaging portion provided in the first deflection region moves and illustrating an action of the elongated member depicted in FIG. 1.

As depicted in FIGS. 6A to 6C, the engaging portion 40 is permitted to move to a first position P1 (refer to FIG. 6B) and a second position P2 (refer to FIG. 6C) by the gap g. At the first position P1, the first abutting portion 41 of the engaging portion 40 abuts with the first guide face 31 of the guide portion 15 and besides the fourth abutting portion 44 of the engaging portion 40 abuts with the fourth guide face 34 of the guide portion 15. At the second position P2, the second abutting portion 42 of the engaging portion 40 abuts with the second guide face 32 of the guide portion 15 and besides the third abutting portion 43 of the engaging portion 40 abuts with the third guide face 33 of the guide portion 15. For example, if the engaging portion 40 moves toward the first position P1 as depicted in FIG. 6B, then a deflection motion in which the elongated member 10 is deflected in one direction (to the lower side in FIG. 1) is carried out. However, if the engaging portion 40 moves toward the second position P2 as depicted in FIG. 6C, then a deflection motion in which the elongated member 10 is deflected in the other direction (to the upper side in FIG. 1) is carried out.

Further, as depicted in FIGS. 6A to 6C, in the present embodiment, the first guide face 31 and the second guide face 32 of the guide portion 15 of the deflection mechanism 20 are formed in an inclined relationship along a circumferential direction with respect to the axial line C. The first abutting portion 41 and the second abutting portion 42 of the engaging portion 40 are configured so as to have a face shape formed so as to abut at least at part thereof with the first and second guide faces 31 and 32, respectively. In the following description of the present embodiment, the first to fourth abutting portions are represented as first to fourth engaging faces 41 to 44.

Referring to FIGS. 1 and 3, the elongated member 10 can be configured, for example, from a hollow tube material to which various processes are performed. The tube material may be comprised of, for example, a metal material, a hard resin material and so forth can be used. The metal material may include, for example but is not limited to, stainless steel, nickel-titanium alloy or the like can be used. The resin material may include, for example but is not limited to, hard polyethylene such as polypropylene (PP), high-density polyethylene (HDPE), polyethylene terephthalate (PET), or polybutylene terephthalate (PBT), hard urethane, polyimide (PI), polystyrene, polyether ether ketone (PEEK), polyamide, polyether imide, polyamide-imide, modified polyphenyleneether, polycarbonate or the like. Further, for the tube material, for example, a tube material of a cylindrical shape on which a distal end opening 11, a proximal end opening 13, and a lumen 14 extending from the distal end opening 11 to the proximal end opening 13 are formed can be used.

The deflection mechanism 20 provided on the elongated member 10 can be formed by forming a slit of a predetermined shape which extends from an outer face to an inner face (or from an inner face to an outer face) on the tube material. A working method for forming the slit can be suitably selected in accordance with a nature of a material to be used and is not limited particularly. However, a known method such as, for example, laser processing or etching can be selectively used.

The guide portion 15 signifies a portion of the elongated member 10 at which the grooved portion 30 is formed. Further, the supporting portion 18 is configured from portions at which the guide portion 15 and the engaging portion 40 contact with and support each other, and in the present embodiment, from a base point 37 of the guide portion 15 and a base point 47 of the engaging portion 40 hereinafter described.

The dimension in the longitudinal direction, inner diameter, outer diameter and so forth, of the elongated member 10 can be designed in accordance with the usage of the elongated member 10, specifications of a product to which the elongated member 10 is applied and so forth and is not limited particularly. However, for example, the elongated member 10 can be formed so as to have a length of 50 to 1000 mm, an inner diameter of 1 to 5 mm and an outer diameter of 2 to 6 mm.

The elongated member 10 is configured such that it can be deflected over a predetermined range in the longitudinal direction by disposing a plurality of deflection mechanisms 20 at positions different from each other in the longitudinal direction. Further, in order to allow different portions of the elongated member 10 to be deflected with different curvatures from each other, a plurality of deflection regions 100, 200 and 300 are provided on the elongated member 10.

The first deflection region 100 is a region formed at the distal end side of the elongated member 10 and is a portion which allows the elongated member 10 to be deflected by a comparatively high curvature. The second deflection region 200 is a region formed on the proximal end side of the elongated member 10 with respect to the first deflection region 100 and is formed, in the present embodiment, over a predetermined range from the proximal end portion of the elongated member 10. The second deflection region 200 makes it possible for the elongated member 10 to be deflected by a curvature smaller than that of the first deflection region 100. The different deflection region 300 is formed between the first deflection region 100 and the second deflection region 200 and is a portion which allows the elongated member 10 to be deflected by a curvature smaller than that of the first deflection region 100 but greater than that of the second deflection region 200.

Since the relationship of the curvatures of the deflection regions 100, 200 and 300 in the elongated member 10 is set in such a manner as described above, a deflection motion is carried out such that the curvature gradually decreases from the distal end side to the proximal end side. By the deflection regions 100, 200 and 300, such predetermined functions as described below are provided to the elongated member 10. The distal end side of the elongated member 10 has a great deflectable range such that it is deformed following the shape of a biological organ or the like. In this manner, it is easy for the distal end side of the elongated member 10 to reach a target peripheral position in a living body. The second deflection region 200 deflects the elongated member 10 by a comparatively small curvature. Therefore, the second deflection region 200 functions as a shaft portion which suitably transmits push-pull force provided by an operation on the hand side to the distal end side. The different deflection region 300 has a function as a shaft portion and further makes it possible to deflect the elongated member 10 by a predetermined curvature on the backbone side (central side) of the living body on which such a high curvature as is required in a peripheral position in the living body is not required.

The dimensions of the deflection regions 100, 200 and 300 in the longitudinal direction can be designed suitably in accordance with a usage and so forth of the elongated member 10 and are not limited particularly. However, in the present embodiment, the length of the first deflection region 100 is in the range of approximately 10 to approximately 100 mm; the length of the second deflection region 200 is in the range of approximately 20 to approximately 200 mm; and the length of the different deflection region 300 is in the range of approximately 20 to approximately 700 mm.

In the following description, a deflection mechanism, a grooved portion and an engaging portion formed in the first deflection region 100 are referred to as first deflection mechanism 20, first grooved portion 30 and first engaging portion 40, respectively. A deflection mechanism, a grooved portion and an engaging portion formed in the second deflection region 200 are referred to as second deflection mechanism 220, second grooved portion 230 and second engaging portion 240, respectively. A deflection mechanism, a grooved portion and an engaging portion formed in the different deflection region 300 are referred to as third deflection mechanism 320, third grooved portion 330 and third engaging portion 340, respectively.

Referring to FIGS. 3 and 6A, the first guide face 31 and the second guide face 32 of the first grooved portion 30 formed in the first deflection region 100 are formed in an inclined relationship to the distal end side in the longitudinal direction of the elongated member 10. The first engaging face 41 and the second engaging face 42 of the first engaging portion 40 are formed in an inclined relationship to the distal end side in the longitudinal direction of the elongated member 10.

The angle by which the first guide face 31 and the second guide face 32 of the first grooved portion 30 of the guide portion 15 are inclined with respect to the axial line C may be, for example, 5 to 30 degrees in the plan views depicted in FIGS. 3 and 6A. The distal end shape of the first grooved portion 30 formed by connection of the first guide face 31 and the second guide face 32 is a substantially V shape in which the base point 37 at which the first guide face 31 and the second guide face 32 merge is formed on the axial line C.

The third guide face 33 and the fourth guide face 34 of the first grooved portion 30 of the guide portion 15 are formed such that they extend in an inclined relationship with respect to the axial line C. The angle by which the third guide face 33 and the fourth guide face 34 are inclined with respect to the axial line C can be, for example, 5 to 30 degrees as viewed in the plan view of FIG. 6A.

A fifth guide face 35 is formed on the first grooved portion 30 of the guide portion 15 such that it continues to the first guide face 31 and the third guide face 33. The fifth guide face 35 is formed in an inclined relationship by a predetermined angle from the first guide face 31 side to the third guide face 33 side. Further, a sixth guide face 36 is formed on the first grooved portion 30 such that it continues to the second guide face 32 and the fourth guide face 34. The sixth guide face 36 is formed in an inclined relationship by a predetermined angle from the second guide face 32 side to the fourth guide face 34 side.

The first engaging portion 40 is formed slightly smaller than the first grooved portion 30 and is disposed so as to be accommodated in the first grooved portion 30. The angle by which the first engaging face 41 and the second engaging face 42 of the first engaging portion 40 are inclined with respect to the axial line C is set smaller than the angle by which the first guide face 31 and the second guide face 32 of the first grooved portion 30 are inclined with respect to the axial line C and can be, for example, 0 to 25 degrees as viewed in the plan view of FIG. 6A. A distal end shape of the first engaging portion 40 formed by the connection of the first engaging face 41 and the second engaging face 42 is a substantially V shape in which the base point 47 at which the first engaging face 41 and the second engaging face 42 merge is formed on the axial line C.

The third engaging face 43 and the fourth engaging face 44 of the first engaging portion 40 are formed such that they extend in an inclined relationship with respect to the axial line C. The angle by which the third engaging face 43 and the fourth engaging face 44 are inclined with respect to the axial line C is set smaller than the angle by which the third and fourth guide faces 33 and 34 of the first grooved portion 30 are inclined with respect to the axial line C and can be set, for example, to 0 to 25 degrees on the plan view of FIG. 6A.

A fifth engaging face 45 of the first engaging portion 40 is formed in a continuing relationship to the first engaging face 41 and the third engaging face 43 and is inclined by a predetermined angle from the first engaging face 41 side to the third engaging face 43 side.

A sixth engaging face 46 of the first engaging portion 40 is formed in a continuing relationship to the second engaging face 42 and the fourth engaging face 44 and is inclined by a predetermined angle from the second engaging face 42 side to the fourth engaging face 44 side similarly to the fifth engaging face 45.

As depicted in FIG. 3, a first extension 48 is formed at the proximal end of the first engaging portion 40 formed in the first deflection region 100 such that it continues to the first deflection mechanism 20 neighboring therewith in the longitudinal direction. Correspondingly, a second extension 49 is formed on the first deflection mechanism 20 such that it extends in a circumferential direction and continues to the first deflection mechanism 20 neighboring therewith in a circumferential direction. The first deflection region 100 is configured such that a plurality of deflection mechanisms 20 are connected to each other by the extensions 48 and 49.

In the first deflection region 100, a plurality of first grooved portions 30 and a plurality of first engaging portions 40 are formed at positions different from each other in a circumferential direction (upward and downward direction in FIG. 3) of the elongated member 10. Further, for example, two first grooved portions 30 and two first engaging portions 40 can be disposed at positions same as each other in the longitudinal direction but displaced by 180 degrees in the circumferential direction such that the first grooved portions 30 and the first engaging portions 40 are individually opposed to each other on the circumference.

The first grooved portions 30 formed at the different positions in the circumferential direction are communicated with each other through a side groove 50 extending in the circumferential direction of the elongated member 10. By forming the plurality of first grooved portions 30 and the plurality of first engaging portions 40 at different positions from each other in the circumferential direction such that the first grooved portions 30 are communicated with each other by the side groove 50, the range over which the first deflection region 100 can move in the circumferential direction can be expanded, and a deflection motion of the elongated member 10 can be commenced smoothly by lower force.

The shape of the side groove 50 may be, for example, a substantially elliptical shape in which the width of the side groove 50 gradually increases from the side of one of the first grooved portions 30 disposed adjacent in the circumferential direction to the side of the other first grooved portion 30 and gradually decreases from the middle.

Figure 7A:
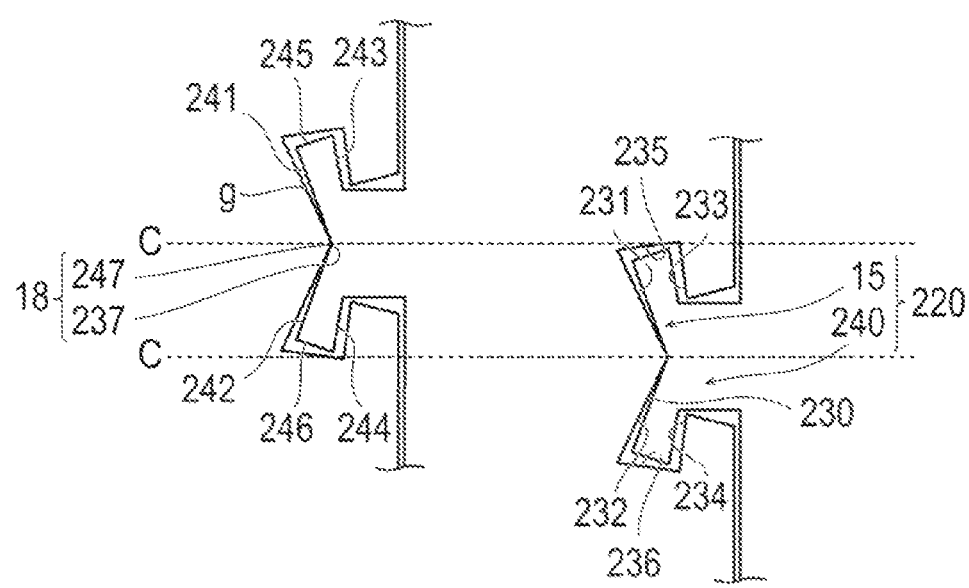
FIG. 7A is a plan view depicting, in an enlarged scale, a guide portion and an engaging portion provided in a second deflection region and illustrating an action of the elongated member depicted in FIG. 1.

With reference to FIGS. 4 and 7A, a first guide face 231 and a second guide face 232 of the second grooved portion 230 formed on the second deflection region 200 are formed in an inclined relationship to the distal end side in the longitudinal direction of the elongated member 10. Also a first engaging face 241 and a second engaging face 242 of the second engaging portion 240 are formed in an inclined relationship to the distal end side in the longitudinal direction of the elongated member 10. Also in the second deflection region 200, a plurality of second grooved portions 230 and a plurality of second engaging portions 240 can be formed in a circumferential direction of the elongated member 10 similarly as in the case of the first deflection region 100.

As depicted in FIG. 4, in the second deflection region 200, the spacing distance d2 between the second deflection mechanisms 220 neighboring with each other in the longitudinal direction is set greater than the spacing distance d1 between the first deflection mechanisms 20 positioned adjacent each other in the longitudinal direction in the first deflection region 100 (refer to FIG. 3).

By setting the spacing distance d2 in the second deflection region 200 greater than the spacing distance d1 in the first deflection region 100 in this manner, the curvature when the second deflection region 200 is deflected can be made smaller than the curvature when the first deflection region 100 is deflected without carrying out such design as to change the shape of the second grooved portion 230 or the shape of the second engaging portion 240 from the shape of the first grooved portion 30 or the shape of the first engaging portion 40 formed in the first deflection region 100.

The shape of the second grooved portion 230 and the second engaging portion 240 formed in the second deflection region 200 can be configured similarly to those of the first grooved portion 30 and the first engaging portion 40 formed in the first deflection region 100. However, in the second deflection region 200, it is omitted to form the first extension 48 continuing to and between the second deflection mechanisms 220 neighboring with each other in the longitudinal direction or the second extension 49 continuing to and between the second deflection mechanisms 220 neighboring with each other along the circumferential direction. Further, as depicted in FIG. 4, the supporting portion 18 is configured from a base point 237 formed on the guide portion 15 and a base point 247 formed on the second engaging portion 240.

In the second deflection region 200, at least one set of second deflection mechanisms 220 neighboring with each other in the longitudinal direction of the elongated member 10 is disposed in such a manner that they are arranged at positions different from each other in the circumferential direction (upward and downward direction in FIG. 4). Where the second deflection mechanisms 220 neighboring with each other in the longitudinal direction are disposed at positions displaced from each other in the circumferential direction, and since movement of the second engaging portion 240 is permitted at a plurality of locations in the circumferential direction, the elongated member 10 is configured so as to be more deflectable.

Since the curvature of the second deflection region 200 when it is deflected is smaller than the curvature of the first deflection region 100, the number of second grooved portions 230 to be provided is relatively smaller than the number of first grooved portions 30 of the first deflection region 100 to be provided. Therefore, the second deflection region 200 is formed such that it has a comparatively high rigidity. However, where a plurality of second deflection mechanisms 220 are provided at positions displaced from each other in the circumferential direction as described above, the rigidity can be prevented from being set to an excessively high level.

Although the phase of the second deflection mechanisms 220 in the circumferential direction is not limited particularly, it can be set such that, for example, the phases of the second deflection mechanisms 220 neighboring with each other are displaced by 90 degrees from each other. It is to be noted that, in order to achieve an effect by such positional displacement in the circumferential direction as described above, only it is only necessary for at least one set of the second deflection mechanisms 220 neighboring with each other to be disposed in such a manner that they are positioned at positions different from each other in the circumferential direction but it is not necessary for all neighboring second deflection mechanisms 220 of the second deflection region 200 to be disposed at different positions from one another in the circumferential direction.

Figure 8A:
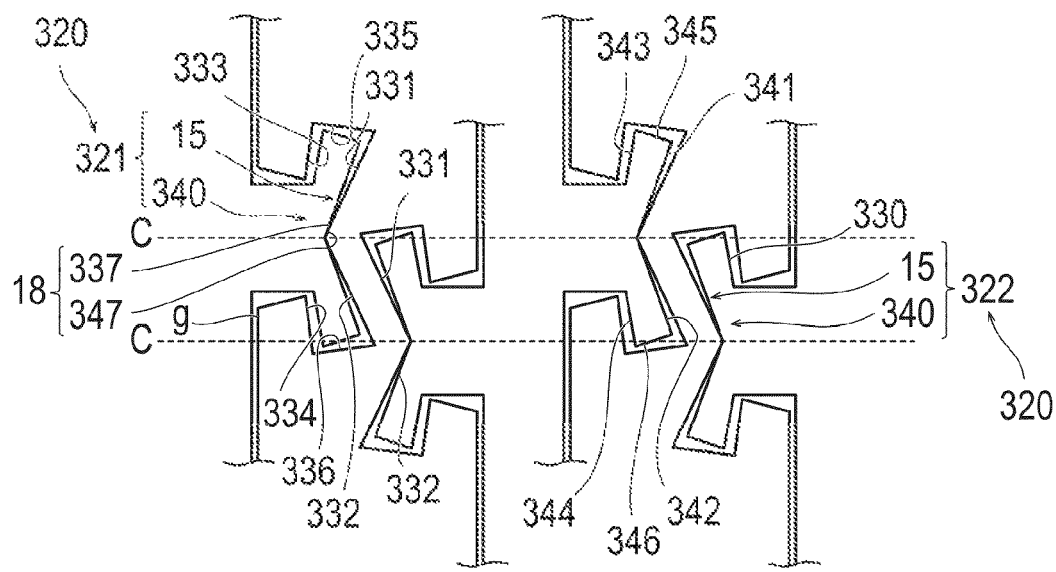
FIG. 8A is a plan view depicting, in an enlarged scale, a guide portion and an engaging portion provided in a different deflection region and illustrating an action of the elongated member depicted in FIG. 1.

As depicted in FIGS. 5 and 8A, in the different deflection region 300, the third grooved portions 330 of at least one set of the third deflection mechanisms 320 neighboring with each other in the longitudinal direction of the elongated member 10 are disposed in an opposing relationship to each other. It is to be noted that, in the present embodiment, the different deflection region 300 is configured such that it has a proximal end inclined deflection mechanism 321 in which first and second guide faces 331 and 332 of the third grooved portion 330 and first and second engaging faces 341 and 342 of the third engaging portion 340 are inclined to the proximal end side in the longitudinal direction of the elongated member 10 and a distal end inclined deflection mechanism 322 in which the first and second guide faces 331 and 332 of the third grooved portion 330 and the first and second engaging faces 341 and 342 of the third engaging portion 340 are inclined to the distal end side in the longitudinal direction of the elongated member 10.

Figure 8B:
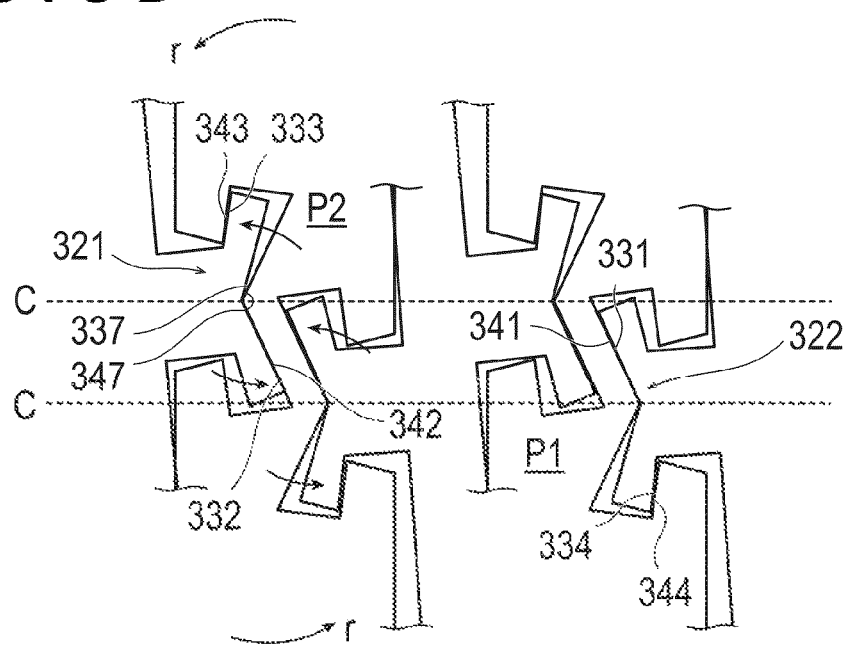
FIG. 8B is a plan view depicting, in an enlarged scale, a manner in which the engaging portion provided in the different deflection region moves and illustrating an action of the elongated member depicted in FIG. 1.
Figure 8C:
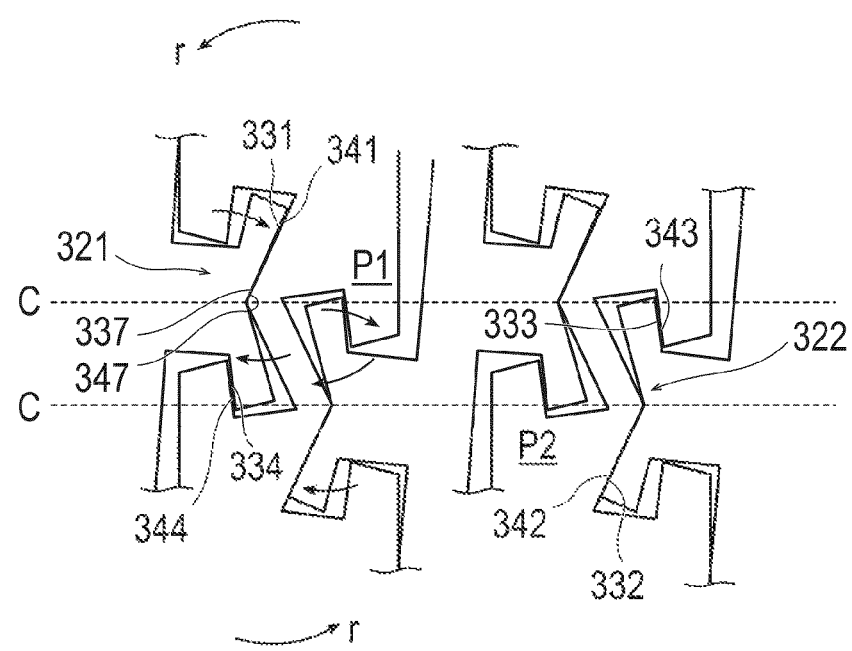
FIG. 8C is a plan view depicting, in an enlarged scale, another manner in which the engaging portion provided in the different deflection region moves and illustrating an action of the elongated member depicted in FIG. 1.

As depicted in FIGS. 8B and 8C, in the different deflection region 300 configured in such a manner as described above, it is possible to dispose the proximal end inclined deflection mechanism 321 and the distal end inclined deflection mechanism 322 neighboring with each other such that the distance therebetween is very small. Therefore, in the different deflection region 300, a deflection motion of the elongated member 10 can be started smoothly by lower force.

The shape of the third grooved portion 330 and the third engaging portion 340 of the distal end inclined deflection mechanism 322 can be configured similarly to that of the first grooved portion 30 and the first engaging portion 40 formed in the first deflection region 100, respectively. As depicted in FIG. 5, the proximal end inclined deflection mechanism 321 is shaped such that the distal end inclined deflection mechanism 322 is reversed with respect to the reference axis e which is orthogonal to the axial line C. Further, as depicted in FIG. 5, the supporting portion 18 is configured from a base point 337 formed on the guide portion 15 and a base point 347 formed on the third engaging portion 340.

As depicted in FIG. 5, the spacing distance d3 between the proximal end inclined deflection mechanisms 321 neighboring with each other in the longitudinal direction can be set greater than the spacing distance d1 between the first deflection mechanisms 20 neighboring with each other in the longitudinal direction. Further, the spacing distance d4 between the distal end inclined deflection mechanisms 322 neighboring with each other in the longitudinal direction in the different deflection region 300 is set greater than the spacing distance d1 between the first deflection mechanisms 20 neighboring with each other in the longitudinal direction in the first deflection region 100. Since the spacing distances d3 and d4 between the third deflection mechanisms 320 neighboring with each other in the different deflection region 300 are set in this manner, the curvature when the different deflection region 300 is deflected is smaller than the curvature of the first deflection region 100 similarly to the second deflection region 200.

It is to be noted that, as depicted in FIG. 5, in the different deflection region 300, a plurality of third grooved portion 330 and a plurality of third engaging portions 340 are also formed in a circumferential direction of the elongated member 10 similarly as in the first and second deflection regions 100 and 200. In addition, at least one set of the third deflection mechanisms 320 which neighbor with each other in the longitudinal direction can be configured in such a manner that they are disposed at positions different from each other in the circumferential direction of the elongated member 10 similarly as in the second deflection region 200.

As depicted in FIG. 2, the operating member 70 for causing a deflection motion of the elongated member 10 to be carried out and canceling the deflection motion of the elongated member 10 to deform the elongated member 10 into a linear state is attached to the elongated member 10.

The operating member 70 can be attached, for example, to an attaching portion 80 formed on the elongated member 10. The attaching portion 80 can be configured such that it has, for example, a fixing portion 81 in the form of a groove disposed on the distal end side of the elongated member 10 and a threading groove 83 extending from the distal end side to the proximal end side of the elongated member 10.

The operating member 70 can be configured from a push-pull member which, in one example, when it is subjected to a pushing or pulling operation in the longitudinal direction of the elongated member 10, deflects the elongated member 10 or deforms the elongated member 10 into a linear state. While the push-pull member 70 can be configured, for example, from a known string-like member as depicted in FIG. 2, it can also be configured also from a wire, a flexible plate member, or the like as would be known to those having ordinary skill in the art. Attachment of the push-pull member 70 to the elongated member 10 can be carried out by disposing and fixing the push-pull member 70 in the fixing portion 81 and then disposing and fixing the push-pull member 70 also in the threading groove 83. Where the push-pull member 70 is fixed in this manner, it can be pulled to start a deflection motion of the elongated member 10, and the pulling force can be loosened to cancel the deflection motion to allow the elongated member 10 to be deformed so as to have a linear shape.

The threading groove 83 can be formed, for example, at a position different from the positions at which the grooved portions 30, 230 and 330 and the engaging portions 40, 240 and 340 are formed on the elongated member 10. In the example depicted in FIG. 2, the threading groove 83 is disposed at a position displaced from the positions, at which the grooved portions 30, 230 and 330 and the engaging portions 40, 240 and 340 are formed, by 90 degrees in the circumferential direction. By such disposition, when the engaging portions 40, 240 and 340 are moved to carry out a deflection motion, the engaging portions 40, 240 and 340 and the push-pull member 70 can be prevented from interfering with each other. However, in the elongated member 10, the position at which the push-pull member (operating member) 70 is disposed is not limited to a position in the threading groove 83. For example, the push-pull member 70 can be disposed in the lumen 14 of the elongated member 10.

A fixation assisting portion 85 for fixing, for example, the push-pull member 70 to the elongated member 10 with a higher degree of certainty can be provided on the fixing portion 81. The fixation assisting portion 85 can be configured from a groove formed so as to extend in the circumferential direction of the elongated member 10 by a predetermined length from the fixing portion 81. By carrying out fixation in a state in which the push-pull member 70 is positioned so as to be locked by the fixation assisting portion 85, the push-pull member 70 can be fixed with a higher degree of certainty to the elongated member 10.

In another embodiment, two push-pull members 70 can be attached at positions displaced, for example, by 180 degrees from each other in the circumferential direction of the elongated member 10. Where this configuration is adopted, the push-pull members 70 can be configured such that the elongated member 10 is moved in one direction (toward the lower side in FIG. 1) by pulling one of the push-pull members 70 whereas the elongated member 10 is moved in the other direction (to the upper side in FIG. 1) by pulling the other push-pull member 70.

With regard to the method for fixing the push-pull member 70 to the elongated member 10, an arbitrary method can be selected in accordance with the materials of the elongated member 10 and the push-pull member 70. For example, a method of disposing the push-pull member 70 on the fixing portion 81 and embedding the push-pull member 70 using a bonding agent made of resin or thermal fusion bonding can be adopted.

As depicted in FIG. 1, the elongated member 10 can include an elastic member 60 which covers the outer surface of the operating member 70 disposed in the threading groove 83 and the elongated member 10.

Further, the elongated member 10 may be used as a member for introducing various other members, media, processing tools, devices and the like through the lumen 14 of the elongated member 10. For example, by threading an endoscope or similar instrument of a small diameter into the lumen 14 of the elongated member 10, a device can be operated to a target position while confirmation is carried out with the eyes. Further, by replacing the endoscope with a processing tool such as a biopsy device at the target position, the tissue can be sampled through the lumen 14 of the elongated member 10. Additionally, by threading, for example, an ultrasonic diagnostic device into the lumen 14 of the elongated member 10, observation of the target region can be carried out particularly. Moreover, by inserting a tubular body (catheter) of a small diameter into the elongated member 10, the tubular body can be transported to a peripheral region of a biological organ. As a result, such a treatment action as drug application can be carried out from a position in the proximity of the target tissue. Furthermore, for example, by selecting a predetermined treatment device as a processing tool and threading the treatment device into the elongated member 10, it is possible to carry out a treatment action for the target region. As the treatment device, for example, an ablation device (cryo catheter), a high frequency ablation catheter, a microwave ablation catheter, a photodynamic therapy (PDT) probe and similar like instruments can be used.

In the lumen 14 of the elongated member 10, a tubular member configured from a resin member not depicted is threaded in a closely contacting relationship with the inner surface of the lumen 14. Consequently, it is possible to raise the efficiency in suction utilizing the lumen 14 and reduce the frictional resistance between the members described above and the lumen 14.

When the elongated member 10 is used in such a manner as described above, it is necessary to prevent fluid such as body fluid or various kinds of media from flowing to the inside and the outside of the elongated member 10 through the grooved portions 30, 230 and 330. Therefore, the tubular elastic member 60 serving as a hull of the elongated member 10 covers the outer surface of the elongated member 10. By using the elastic member 60 as a cover, the suction efficiency of body fluid, secretion and so forth from the distal end opening 11 of the elongated member 10 can be improved. In addition, this allows the introduction of drugs from the proximal end opening 13, or the like. Further, by covering the elongated member 10 with the elastic member 60, protection of the elongated member 10 and protection of a living body of an introduction target can be achieved. Since elasticity is provided to the elongated member 10, the elongated member 10 can be configured so as to be deformed elastically. In addition, the operating member 70 can be suitably preventing from coming off the threading groove 83.

Examples of the material for configuring the elastic member 60 used to cover the elongated member 10 includes, but are not limited to, polyolefin such as polyethylene (PE) or polypropylene (PP), polyester such as polyethylene terephthalate (PET), polyamide (PA), polyimide (PI), polyamide-imide (PAI), silicone, polyurethane (PU), ethylene-vinyl acetate copolymer (EVA), polyvinyl chloride (PVC), polytetrafluoroethylene (PTFE), polyvinylidene fluoride (PVDF), a fluorine-based resin such as perfluoroalkoxy fluorine resin (PFA), a thermoplastic resin such as thermoplastic elastomer and so forth.

A hydrophilic material or a hydrophobic material can be added to the outer surface of the elastic member 60 and/or the outer surface of the elongated member 10.

Examples of the hydrophilic material include, but are not limited to, a cellulose polymer substance, a polyethylene oxide polymer substance, a maleic anhydride polymer substance (for example, maleic anhydride copolymer such as methyl vinyl ether-maleic anhydride copolymer), an acrylamide polymer substance (for example, block copolymer of polyacrylamide, polyglycidyl methacrylate-dimethyl acrylamide (PGMA-DMAA), water-soluble nylon, polyvinyl alcohol, polyvinylpyrrolidone and so forth. Such hydrophilic materials as described above in most cases exhibit lubricity by humidity (water absorption) and reduce the frictional resistance (sliding resistance) of the inner wall of a wet biological organ. Consequently, the sliding performance of the elongated member 10 is improved and the operability is further improved.

On the other hand, examples of the hydrophobic material may include, but are not limited to, polyamide, polyimide, polyurethane, polystyrene, silicone resins, fluorine-based resins (PTFE, tetrafluoroethylene-ethylene copolymer (ETFE) and so forth) and composite materials of the materials. Even where such hydrophobic materials as just mentioned are used, effects similar to those achieved by the hydrophilic materials described above can be exhibited.

A motion of the deflection mechanism formed in each deflection region is now described.

First, the first deflection mechanism 20 formed in the first deflection region 100 is described.

As depicted in FIG. 6A, before the first deflection region 100 is deflected, the base point 47 of the first engaging portion 40 is disposed so as to abut with the base point 37 of the first grooved portion 30. Further, since the first engaging portion 40 is placed in a loosely fitted state due to the gap g between the first grooved portion 30 and the first engaging portion 40, the first deflection region 100 configures a deformable linear shape.

By pulling a predetermined push-pull member 70 (not depicted) in order to deflect the elongated member 10, the first deflection region 100 is deflected in one direction (to the lower side) as depicted in FIG. 6B (the deflection motion is represented by an arrow mark r in FIG. 6B). Thereupon, a movement (pivotal movement) of the first engaging portion 40 is started while the base point 37 of the first grooved portion 30 and the base point 47 of the first engaging portion 40 serve as a fulcrum. Since the movement of the first engaging portion 40 is started around the fulcrum provided by the base portions 37 and 47, it is possible to start the movement of the first engaging portion 40 by lower pulling force. Further, it is possible to start the movement of the first engaging portion 40 smoothly following the pulling operation.

If the push-pull member 70 is operated, then the first engaging portion 40 moves to the first position P1 (shown in FIG. 6B) at which the first engaging face 41 of the first engaging portion 40 abuts with the first guide face 31 of the first grooved portion 30, and the fourth engaging face 44 of the first engaging portion 40 abuts with the fourth guide face 34 of the first grooved portion 30. Then, rotational moment generated by the movement of the first engaging portion 40 is transmitted through two faces including the first engaging face 41 and the fourth engaging face 44 positioned on a diagonal line. Therefore, it is possible to transmit the pulling force provided to the elongated member 10 efficiently along the longitudinal direction in order to deflect the elongated member 10. Further, the state in which the elongated member 10 is deflected is maintained in a state in which the first engaging face 41 of the first engaging portion 40 contacts with the first guide face 31 of the first grooved portion 30, and the fourth engaging face 44 of the first engaging portion 40 contacts with the fourth guide face 34 of the first grooved portion 30. Therefore, the deflection shape of the elongated member 10 can be held suitably, and it can be prevented with certainty that an inadvertent change in shape occurs upon a deflection motion.

By pulling a predetermined push-pull member 70 (not depicted), the first deflection region 100 is deflected in the other direction (to the upper side) as depicted in FIG. 6C. Similarly as in the case described hereinabove with reference to FIG. 6B, the movement (pivotal movement) of the first engaging portion 40 is started around the fulcrum provided by the base point 37 of the first grooved portion 30 and the base point 47 of the first engaging portion 40. Therefore, the movement of the first engaging portion 40 can be started by lower pulling force, and the movement of the first engaging portion 40 can be started smoothly following the pulling operation.

If the push-pull member 70 is operated, then the first engaging portion 40 moves to the second position P2 (shown in FIG. 6C) at which the second engaging face 42 of the first engaging portion 40 abuts with the second guide face 32 of the first grooved portion 30 and the third engaging face 43 of the first engaging portion 40 abuts with the third guide face 33 of the first grooved portion 30. Similarly as in the case described hereinabove with reference to FIG. 6B, the rotational moment generated by the movement of the first engaging portion 40 is transmitted through two faces including the second engaging face 42 and the third engaging face 43 positioned on a diagonal line. Therefore, the pulling force applied to the elongated member 10 in order to deflect the elongated member 10 can be transmitted efficiently along the longitudinal direction. Then, the state in which the elongated member 10 is deflected in the other direction is maintained in a state in which the second engaging face 42 of the first engaging portion 40 contacts with the second guide face 32 of the first grooved portion 30 and besides the third engaging face 43 of the first engaging portion 40 contacts with the third guide face 33 of the first grooved portion 30. Therefore, the deflection shape of the elongated member 10 can be maintained suitably.

Now, a motion of the second deflection mechanism 220 formed in the second deflection region 200 is described.

As depicted in FIG. 7A, before the second deflection region 200 is deflected, the base point 247 of the second engaging portion 240 is disposed so as to abut with the base point 237 of the second grooved portion 230. Further, since the second engaging portion 240 is placed in a state in which it is loosely fitted in the second grooved portion 230 due to the gap g between the second grooved portion 230 and the second engaging portion 240, the second deflection region 200 configures a deformable linear shape.

Figure 7B:
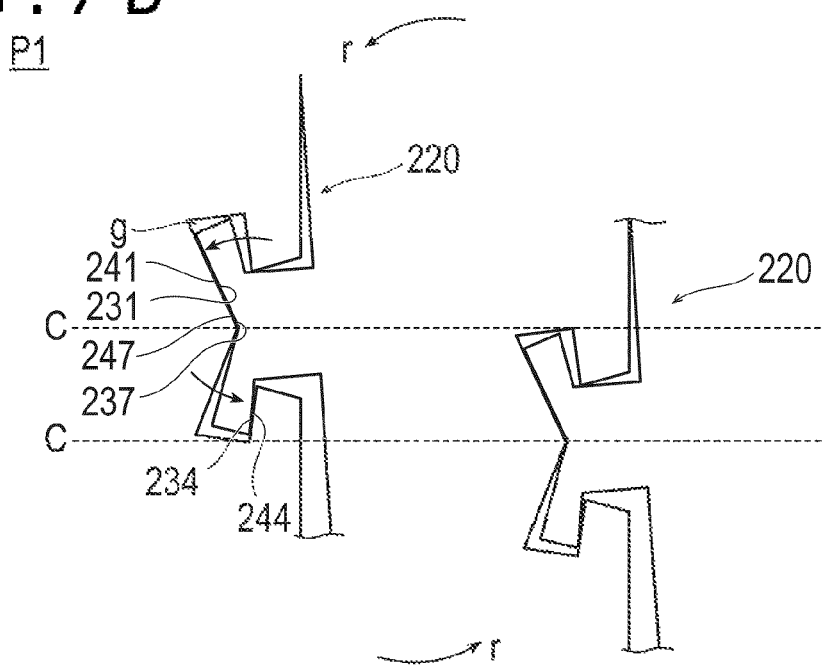
FIG. 7B is a plan view depicting, in an enlarged scale, a manner in which the engaging portion provided in the second deflection region moves and illustrating an action of the elongated member depicted in FIG. 1.

By pulling a predetermined push-pull member 70 (not depicted) in order to deflect the elongated member 10 as depicted in FIG. 7B, the first deflection region 100 is deflected in one direction (to the lower side) (the deflection motion is denoted by an arrow mark r in FIG. 7B). Thereupon, the movement of the second engaging portion 240 is started around the fulcrum provided by the base point 237 of the second grooved portion 230 and the base point 247 of the second engaging portion 240. Further, if the push-pull member 70 (not depicted) is operated, then the first engaging portion 40 is moved to the first position P1 (FIG. 7B) at which the first engaging face 241 of the second engaging portion 240 abuts with the first guide face 231 of the second grooved portion 230 and besides the fourth engaging face 244 of the second engaging portion 240 abuts with the fourth guide face 234 of the second grooved portion 230.

Figure 7C:
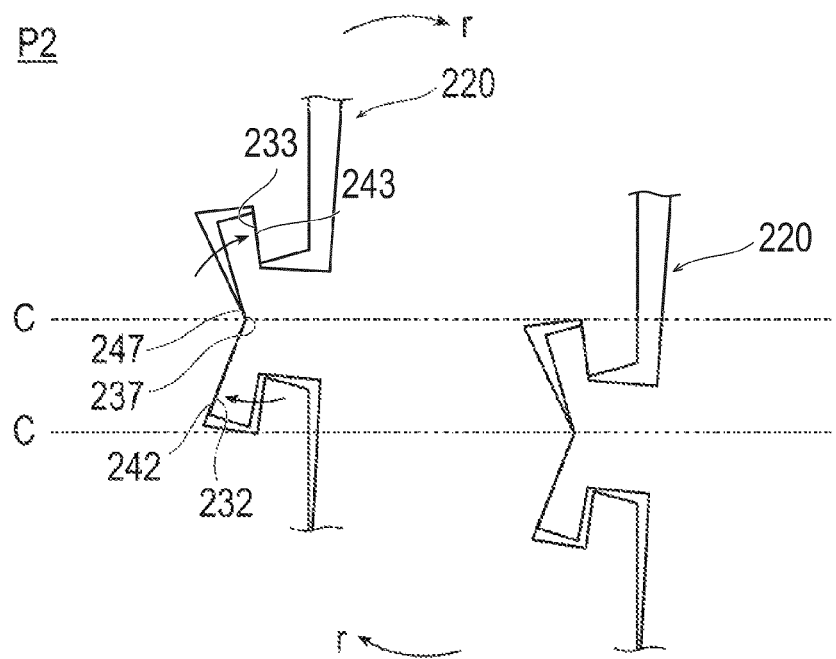
FIG. 7C is a plan view depicting, in an enlarged scale, another manner in which the engaging portion provided in the second deflection region moves and illustrating an action of the elongated member depicted in FIG. 1.

By pulling a predetermined push-pull member 70 (not depicted), the second deflection region 200 is deflected in the other direction (to the upper side) as depicted in FIG. 7C. Thereupon, the movement of the second engaging portion 240 is started around the fulcrum provided by the base point 237 of the second grooved portion 230 and the base point 247 of the second engaging portion 240. Further, if the push-pull member 70 is operated, then the second engaging portion 240 is moved to the second position P2 (FIG. 7C) at which the second engaging face 242 of the second engaging portion 240 abuts with the second guide face 232 of the second grooved portion 230 and besides the third engaging face 243 of the second engaging portion 240 abuts with the third guide face 233 of the second grooved portion 230.

Additionally, when the second deflection region 200 is to be deflected, the movement of the second engaging portion 240 can be started smoothly in the second grooved portion 230 and besides the pulling force applied to the elongated member 10 can be transmitted efficiently along the longitudinal direction similarly as in the case in which the first deflection region 100 is deflected. In addition, the deflection shape of the elongated member 10 can be maintained favorably.

As described hereinabove, the spacing distance d2 between the second deflection mechanisms 220 neighboring with each other in the longitudinal direction in the second deflection region 200 is set greater than the spacing distance d1 between the first deflection mechanisms 20 neighboring with each other in the first deflection region 100. Therefore, when the second deflection region 200 is deflected, the curvature of the deflection is smaller than that in the first deflection region 100 (refer to FIGS. 3 and 4).

A motion of the third deflection mechanism 320 formed in the different deflection region 300 is now described.

As depicted in FIG. 8A, before the different deflection region 300 is deflected, the base point 347 of the third engaging portion 340 is disposed so as to abut with the base point 337 of the third grooved portion 330. Since the third engaging portion 340 is placed in a loosely fitted state due to the gap g between the third grooved portion 330 and the third engaging portion 340, the different deflection region 300 configures a deformable linear shape.

By pulling a predetermined push-pull member 70 (not depicted) in order to deflect the elongated member 10 as depicted in FIG. 8B, the first deflection region 100 is deflected in one direction (to the lower side) (the deflection motion is denoted by an arrow mark r in FIG. 8B). At this time, the movement of the third engaging portion 340 is commenced around the fulcrum provided by the base point 337 of the third grooved portion 330 and the base point 347 of the third engaging portion 340.

If the push-pull member 70 (not depicted) is operated, then on the proximal end inclined deflection mechanism 321 side, the third engaging portion 340 moves to the second position P2 at which the second engaging face 342 of the third engaging portion 340 abuts with the second guide face 332 of the third grooved portion 330 and besides the third engaging face 343 of the third engaging portion 340 abuts with the third guide face 333 of the third grooved portion 330. Meanwhile, in the distal end inclined deflection mechanism 322, the third engaging portion 340 moves to the first position P1 at which the first engaging face 341 of the third engaging portion 340 abuts with the first guide face 331 of the third grooved portion 330 and besides the fourth engaging face 344 of the third engaging portion 340 abuts with the fourth guide face 334 of the third grooved portion 330.

By pulling a predetermined push-pull member 70 (not depicted), the different deflection region 300 is deflected in the other direction (to the upper side) as depicted in FIG. 8C. Thereupon, the movement of the third engaging portion 340 is started around the fulcrum provided by the base point 337 of the third grooved portion 330 and the base point 347 of the third engaging portion 340.

If the push-pull member 70 (not depicted) is operated, then on the proximal end inclined deflection mechanism 321 side, the third engaging portion 340 moves to the second position P2 at which the first engaging face 341 of the third engaging portion 340 abuts with the first guide face 331 of the third grooved portion 330 and besides the fourth engaging face 344 of the third engaging portion 340 abuts with the fourth guide face 334 of the third grooved portion 330. Meanwhile, in the distal end inclined deflection mechanism 322, the third engaging portion 340 moves to the first position P1 at which the second engaging face 342 of the third engaging portion 340 abuts with the second guide face 332 of the third grooved portion 330 and besides the third engaging face 343 of the third engaging portion 340 abuts with the third guide face 333 of the third grooved portion 330.

Also, in the case in which the different deflection region 300 is deflected, the movement of the third engaging portion 340 in the third grooved portion 330 can be started smoothly and besides the pulling force applied to the elongated member 10 can be transmitted efficiently along the longitudinal direction similarly as in the case in which the first and second deflection regions 100 and 200 are deflected. In addition, the deflection shape of the elongated member 10 can be maintained favorably.

As described hereinabove, the spacing distances d3 and d4 (FIG. 5) of the third deflection mechanisms 320 neighboring with each other in the longitudinal direction in the different deflection region 300 are set greater than the spacing distance d1 of the first deflection mechanisms 20 neighboring with each other in the longitudinal direction in the first deflection region 100. Therefore, when the different deflection region 300 is deflected, the curvature of the deflection is smaller than that in the first deflection region 100 (refer to FIGS. 3 and 5).

An action of the elongated member 10 according to the present embodiment is now described.

If predetermined force is applied to the elongated member 10 through the operating member 70 in order to carry out a deflection motion, then the first engaging portion 40 moves around the fulcrum provided by the supporting portion 18 with respect to the guide portion 15 provided in the first deflection mechanism 20, and the movement is transmitted in the longitudinal direction of the elongated member 10. Therefore, the deflection motion of the elongated member 10 can be carried out smoothly. Further, since the range within which the first engaging portion 40 can move can be expanded by the gap g formed between the guide portion 15 and the first engaging portion 40, deformation of the elongated member 10 following the shape of a biological organ or the like can be carried out.

When the first engaging portion 40 moves to the first position P1 and the second position P2 within the first grooved portion 30 provided on the first deflection mechanism 20 until the first and fourth guide faces 31 and 34 of the guide portion 15 and the first and fourth abutting portions 41 and 44 of the first engaging portion 40 are abutted with each other, respectively, or the second and third guide faces 32 and 33 of the guide portion 15 and the second and third abutting portions 42 and 43 of the first engaging portion 40 are abutted with each other, respectively, force is transmitted in the longitudinal direction of the elongated member 10. Since force can be transmitted efficiently in the longitudinal direction of the elongated member 10 through the guide faces and the abutting portions, a deflection motion of the elongated member 10 can be carried out smoothly.

Additionally, since the first and second abutting portions 41 and 42 contact in plane with the first and second guide faces 31 and 32 of the guide portion 15 provided on the first deflection mechanism 20, respectively, force applied to the elongated member 10 can be transmitted further efficiently in the longitudinal direction. Since the deflection shape is kept in the state in which the guide faces and the abutting portions contact in plane with each other, the deflection shape of the elongated member 10 can be maintained suitably. Thus, an inadvertent change in shape can be prevented during a deflection motion.

Moreover, the first and second deflection regions 100 and 200 are formed at positions different from each other in the longitudinal direction of the elongated member 10, and the spacing distance d2 between the second deflection mechanisms 220 neighboring with each other in the longitudinal direction in the second deflection region 200 is set greater than the spacing distance d1 between the first deflection mechanisms 20 neighboring with each other in the longitudinal direction in the first deflection region 100. Therefore, the curvatures at a plurality of locations of the elongated member 10 in the longitudinal direction can be made different from each other to carry out a deflection motion. Accordingly, various types of elongated members 10 suitable for different production specifications such as medical tools can be provided. For example, by providing a portion which is deflected by a comparatively small curvature as in the second deflection region 200 on the proximal end side, the elongated member 10 can be provided with a function as a shaft portion for transmitting push-pull force suitably.

In the different deflection region 300 formed on the elongated member 10, the third grooved portion 330 of the third deflection mechanisms 320 neighboring with each other in the longitudinal direction are disposed in an opposing relationship to each other. Therefore, when the different deflection region 300 is to be deflected, the deflection motion can be started smoothly by lower force.

At least one set of deflection mechanisms 200 or 300 neighboring with each other in the longitudinal direction of the elongated member 10 is disposed in such a manner that they are positioned at positions different from each other in the circumferential direction of the elongated member 10. Therefore, it is possible to permit a movement of the engaging portions 240 or 340 at a plurality of locations in the circumferential direction, and the elongated member 10 can be configured such that it can be further readily deflected.

Further, a plurality of first grooved portions 30 and a plurality of first engaging portions 40 are formed at positions different from each other in the circumferential direction of the elongated member 10, and the first grooved portions 30 are communicated with each other through the side grooves 50 extending in the circumferential direction of the elongated member 10. Therefore, the range within which the components of the elongated member 10 are movable in the circumferential direction can be assured great. Consequently, a deflection motion of the elongated member 10 can be carried out smoothly by lower force.

Since the operating member is configured from the push-pull member 70, the elongated member 10 can be deflected or deformed into a linear state by a simple operation for pushing or pulling the push-pull member 70 along the longitudinal direction of the elongated member 10. Therefore, the elongated member 10 is further improved in convenience in use.

Further, since the push-pull member 70 is disposed in the threading groove 83 formed along the longitudinal direction of the elongated member 10, the elongated member 10 can be configured with a small diameter regardless of the provision of the push-pull member 70.

Since the elastic member 60 for covering the outer surface of the push-pull member 70 disposed in the threading groove 83 and the elongated member 10, circulation of liquid to the inside and the outside of the elongated member 10 through the first grooved portion 30 can be prevented. Further, protection of the elongated member 10 and protection of a living body of an introduction target can be anticipated. In addition, since elasticity is provided to the elongated member 10, the elongated member 10 can be configured so as to be elastically deformable. Furthermore, the push-pull member 70 can be prevented from coming off from the threading groove 83.

Modifications

Modifications to the embodiment described above are now described.

Figure 9A:
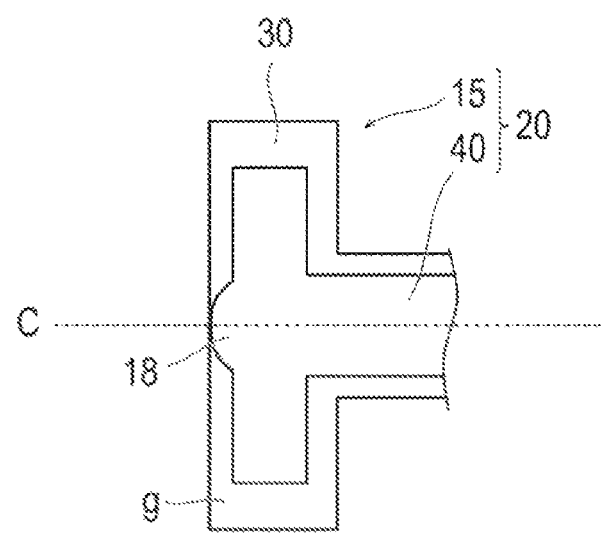
FIG. 9A is a plan view depicting, in an enlarged scale, a guide portion and an engaging portion of an elongated member according to a modification and illustrating an action of the elongated member.
Figure 9B:
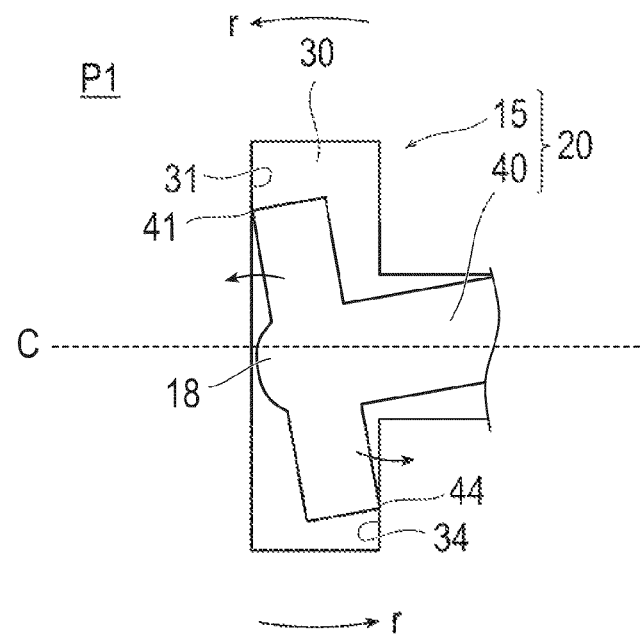
FIG. 9B is a plan view depicting, in an enlarged scale, a manner in which the engaging portion moves and illustrating an action of the elongated member according to the modification.
Figure 9C:
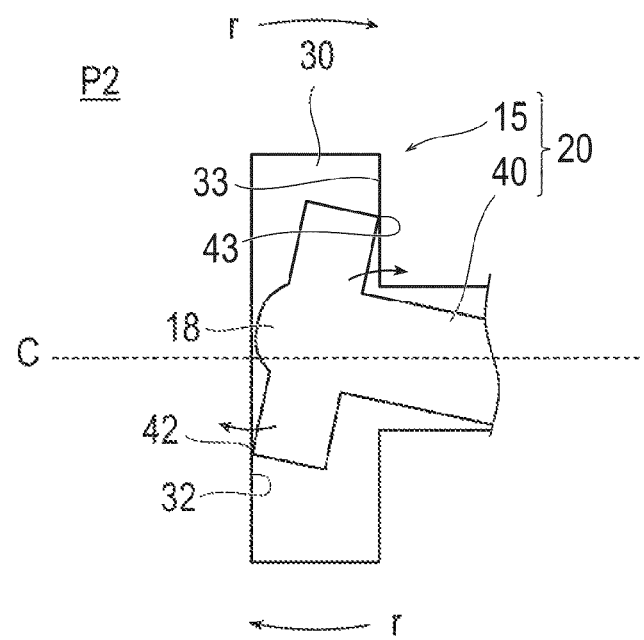
FIG. 9C is a plan view depicting, in an enlarged scale, another manner in which the engaging portion moves and illustrating an action of the elongated member according to the modification.

The shapes of the first grooved portion 30, first engaging portion 40 and supporting portion 18 provided on the guide portion 15 described hereinabove can be altered only if the first engaging portion 40 is supported for movement in the first grooved portion 30. For example, as depicted in FIG. 9A, it is possible to form the shape of the first grooved portion 30 and the first engaging portion 40 in a substantially T shape and configure the supporting portion 18 from a projection formed on the first engaging portion 40. If this configuration is applied, then when the first engaging portion 40 moves to the first position P1 around the fulcrum provided by the supporting portion 18 as depicted in FIG. 9B, the two apexes of the first engaging portion 40 serve as the first abutting portion 41 and the fourth abutting portion 44 and are abutted with the first guide face 31 and the fourth guide face 34, respectively. Similarly as depicted in FIG. 9C, when the first engaging portion 40 moves to the second position P2 around the fulcrum provided by the supporting portion 18, the two apexes of the first engaging portion 40 serve as the second abutting portion 42 and the third abutting portion 43 and are abutted with the second guide face 32 and the third guide face 33, respectively. Accordingly, similarly to the elongated member 10 described hereinabove in connection with the embodiment, force can be transmitted efficiently in the longitudinal direction of the elongated member 10 through the guide faces and the abutting portions. Thus, a deflection motion of the elongated member 10 can be carried out smoothly.

Figure 10A:
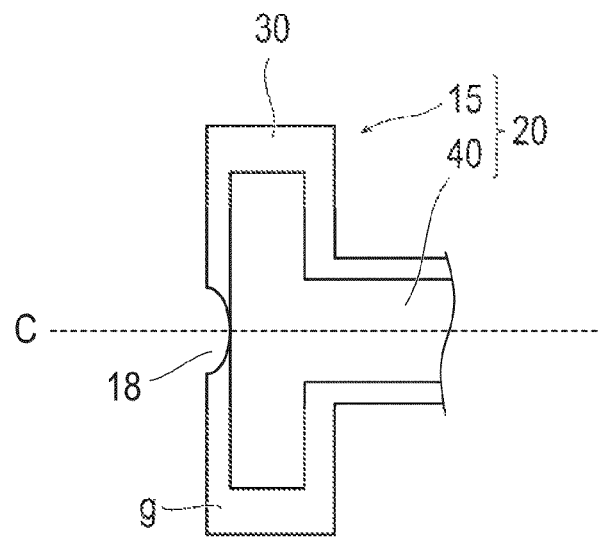
FIG. 10A is a plan view depicting, in an enlarged scale, a guide portion and an engaging portion of an elongated member according to a different modification and illustrating an action of the elongated member.
Figure 10B:
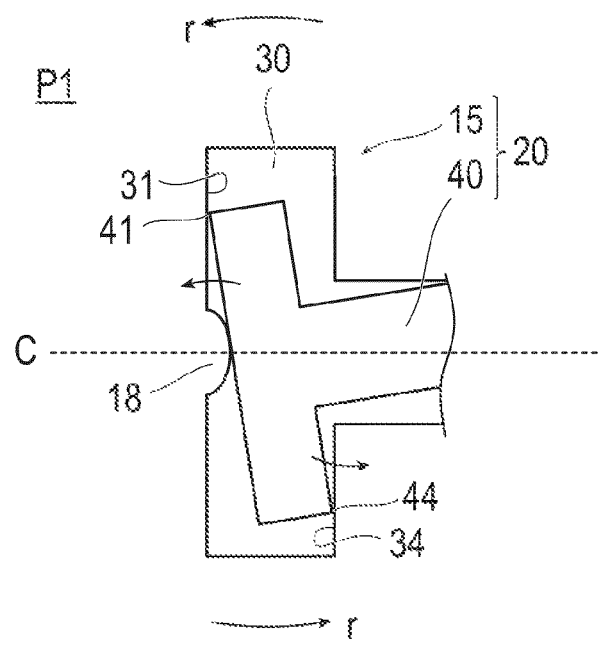
FIG. 10B is a plan view depicting, in an enlarged scale, a manner in which the engaging portion moves and illustrating an action of the elongated member according to the different modification.
Figure 10C:
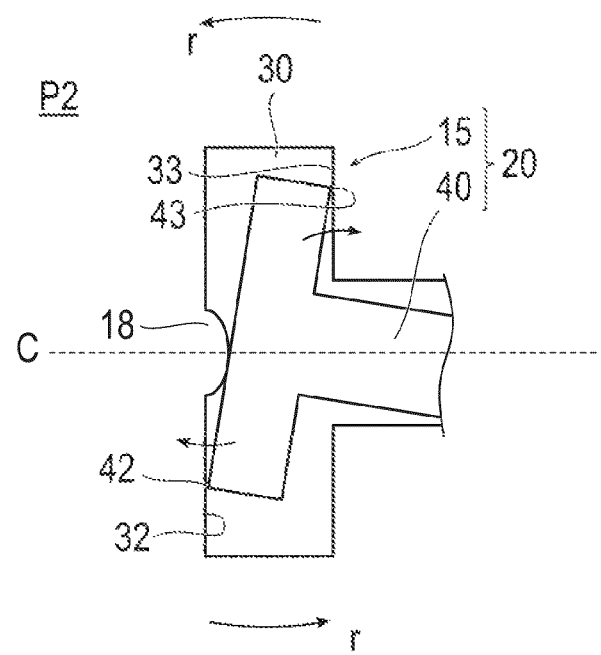
FIG. 10C is a plan view depicting, in an enlarged scale, another manner in which the engaging portion moves and illustrating an action of the elongated member according to the different modification.

Further, it is possible to form the shape of the first grooved portion 30 and the first engaging portion 40 in a substantially T shape and configure the supporting portion 18 from a [projection] formed on the guide portion 15 for example, as depicted in FIG. 10A. Also where the configuration just described is adopted, when the first engaging portion 40 moves to the first position P1 around the fulcrum provided by the first supporting portion 18 as depicted in FIG. 10B, the two apexes of the first engaging portion 40 serve as the first abutting portion 41 and the fourth abutting portion 44 and are abutted with the first guide face 31 and the fourth guide face 34, respectively. Additionally, when the first engaging portion 40 moves to the second position P2 around the fulcrum provided by the supporting portion 18 as depicted in FIG. 10C, the two apexes of the first engaging portion 40 serve as the second abutting portion 42 and the third abutting portion 43 and are abutted with the second guide face 32 and the third guide face 33, respectively. Accordingly, like the elongated members 10 described hereinabove in connection with the embodiment and the modifications, force can be transmitted efficiently in the longitudinal direction of the elongated member 10 through the guide faces and the abutting portions. Consequently, a deflection motion of the elongated member 10 can be carried out smoothly.

While the elongated member according to the present disclosure is described above in connection with the embodiment and the modifications, the present disclosure is not limited to them, but can be modified suitably within the scope of the claims.

For example, the elongated member 10 according to the embodiment is configured such that it includes the first, second and different deflection regions 100, 200 and 300 which are deflected by curvatures different from each other. However, it is possible to configure the elongated member 10 according to the present disclosure such that only one of the deflection regions is provided thereon, or the positions of the deflection regions in the longitudinal direction are changed from those in the embodiment described hereinabove, or else the number of deflection regions is increased. It is also possible to form a deflection mechanism, which is configured from a guide portion and an engaging portion indicated by the modifications in at least one of the deflection regions 100, 200 and 300.

Further, the shapes of the grooved portions and the engaging portions provided on the elongated member 10 are only necessary that at least a predetermined gap is formed between a grooved portion and an engaging portion and permits the engaging portion to move around a fulcrum provided by a supporting portion, and the shapes are not limited to the shapes described hereinabove in connection with the embodiment and the modifications. For example, also it is possible to change the angle by which the first and second guide faces of the guide portion and the first and second engaging faces of the engaging portion are inclined with respect to the axial line, to change the face shape thereof from a flat face to a curved face or to change the inclination direction of the deflection regions with respect to the axial line so as to be inclined in an arbitrary direction to the distal end side or the proximal end side.

In another embodiment a balloon configured for expansion and contraction by injection and discharge of fluid, which is already known in the medical field, can be disposed on the distal end side of the elongated member 10. By expanding the balloon when a drug or the like is to be administered through the elongated member 10, the administration work can be carried out in a state in which the elongated member 10 is positioned fixedly. Therefore, drug administration can be carried out with a higher degree of efficiency. In this case, the balloon may be disposed so as to cover the elastic member 60 or may be disposed directly on the outer surface of the elongated member 10. The balloon is connected to a fluid introduction lumen such that fluid can be introduced into the balloon from the hand side of the balloon, and is expanded when fluid is introduced into the balloon from the fluid introduction lumen. The fluid introduction lumen may be disposed on the outer side of the elongated member 10 or on the inner side of the elongated member 10. The balloon is configured from an expandable material such as, for example, silicone, although the expandable material is not limited to silicone. Consequently, when the balloon is expanded, it closely contacts with a biological lumen, and a work in a state in which the elongated member 10 is fixed to a predetermined position can be carried out. Alternatively, a material which is not expandable, such as nylon or polyethylene, may be disposed in a folded state. Where the elongated member 10 is configured from such materials as described above, a constriction portion appearing in a biological lumen can be expanded.

While the foregoing description of the embodiment exemplifies a configuration wherein the operating member (push-pull member) 70 is disposed in the threading groove 83 of the elongated member 10, the position and so forth for disposition of the operating member 70 can be altered suitably. For example, it is possible to dispose a tubular member in the lumen 14 of the elongated member 10 or outside the elongated member 10 and dispose the operating member 70 in the tubular member. Where such disposition as just described is applied, the sliding performance of the operating member 70 with respect to the elongated member 10 is improved, and therefore, an operation for pushing or pulling the operating member 70 can be carried out smoothly. Where the tubular member is disposed outside the elongated member 10, the tubular member is preferably disposed in the threading groove 83. This makes it possible to reduce the outer diameter of the elongated member 10.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An elongated member which is deflectable and hollow, comprising:
   an operating member configured to deflect the elongated member or deform the elongated member into a linear state; and
   a deflection mechanism at least including a guide portion having a grooved portion formed thereon, an engaging portion engageable with the grooved portion and a supporting portion configured to support the engaging portion for relative movement on the guide portion;
   a gap being formed between the guide portion and the engaging portion so as to allow movement around a fulcrum provided by the supporting portion of the engaging portion in the grooved portion;
   wherein the guide portion at least has a first guide face and a second guide face formed so as to extend outwardly from a longitudinal axis along a longitudinal direction of the elongated member, the first and second guide faces being symmetrical with respect to an axis of symmetry provided by the longitudinal axis,
   a third guide face formed at a position opposing to the first guide face, and a fourth guide face formed at a position opposing to the second guide face;
   the engaging portion at least has first to fourth abutting portions disposed at positions opposing to the first to fourth guide faces, respectively; and
   the engaging portion is held for movement by the gap to a first position at which the first abutting portion abuts with the first guide face and the fourth abutting portion abuts with the fourth guide face and to a second position at which the second abutting portion abuts with the second guide face and the third abutting portion abuts with the third guide face.

2. The elongated member according to claim 1, wherein the deflection mechanism has a face shape formed such that the first and second guide faces are formed in an inclined relationship along a circumferential direction with respect to the longitudinal axis, and the first and second abutting portions abut at least at part thereof with the first and second guide faces, respectively.

3. The elongated member according to claim 1, wherein the elongated member has a deflection region formed such that a plurality of deflection mechanisms are disposed at different positions from each other in the longitudinal direction of the elongated member in the deflection region; and
   the deflection region has a first deflection region, and
   a second deflection region, the second deflection region is formed on a proximal end side of the elongated member with respect to the first deflection region and in which a spacing distance between the deflection mechanisms neighboring with each other in the longitudinal direction is greater than a spacing distance between the deflection mechanisms neighboring with each other in the longitudinal direction in the first deflection region.

4. The elongated member according to claim 3, wherein the deflection region in which the grooved portions of at least a set of one of the deflection mechanisms which neighbor with each other in the longitudinal direction of the elongated member are opposed to each other.

5. The elongated member according to claim 3, wherein at least one set of the deflection mechanisms which neighbor with each other in the longitudinal direction of the elongated member is disposed in such a manner that the deflection mechanisms are positioned at positions different from each other in a circumferential direction of the elongated member.

6. The elongated member according to claim 3, further comprising, a base point of the guide portion, and
   a base point of the engaging portion,
   wherein the supporting portion and engaging portion being configured so that the base point of the guide portion and the base point of the engaging portion remain in contact with each other while the deflection region moves.

7. The elongated member according to claim 1, wherein a plurality of guide portions and a plurality of engaging portions are formed at positions different from each other in a circumferential direction of the elongated member; and
   the grooved portions of the guide portions formed at positions different from each other m the circumferential direction are communicated with each other through a side groove extending in the circumferential direction.

8. The elongated member according to claim 1, wherein the operating member is configured from a pushpull member configured to be subject to a pushing or pulling operation in the longitudinal direction of the elongated member to deflect the elongated member or deform the elongated member into the linear state.

9. The elongated member according to claim 8, wherein the operating member is disposed in a threading groove formed so as to extend in the longitudinal direction of the elongated member.

10. The elongated member according to claim 9, further comprising
    an elastic member configured to cover an outer surface of the operating member disposed in the threading groove and the elongated member.

11. The elongated member according to claim 1, wherein the supporting portion form a substantially v-shape.

12. The elongated member according to claim 1, wherein the engaging portion form a substantially T-shape.

13. The elongated member according to claim 1, wherein the supporting portion is a projection formed on the engaging portion.

14. The elongated member according to claim 1, wherein the supporting portion is a projection formed on the guide portion.

15. The elongated member according to claim 1, wherein the engaging portion moves around a single fulcrum.

16. The elongated member according to claim 1, wherein the fulcrum is centered in the gap between the guide portion and the engaging portion.

17. An elongated member which is deflectable and hollow, comprising:
    an operating member for deflecting the elongated member;
    a deflection mechanism having a plurality of engaging portions and guide portions; and
    a fulcrum configured so that the engaging portion and the guide portion contact with and support each other;
    wherein the engaging portion is formed substantially in the shape of one of a t-shape or y-shape;
    wherein the guide portion is substantially c-shaped and the interior of the c-shaped section defines a grooved portion;
    wherein the grooved portion is configured to pivotally receive and secure the engaging portion;

wherein a gap is formed between the grooved portion and the engaging portion; and wherein the fulcrum is provided in the gap;

wherein the guide portion at least has a first guide face and a second guide face formed so as to extend outwardly from a longitudinal axis along a longitudinal direction of the elongated member, the first and second guide faces being symmetrical with respect to an axis of symmetry provided by the longitudinal axis, a third guide face formed at a position opposing to the first guide face, and a fourth guide face formed at a position opposing to the second guide face;

the engaging portion at least has first to fourth abutting portions disposed at positions opposing to the first to fourth guide faces, respectively; and the engaging portion is held for movement by the gap to a first position at which the first abutting portion abuts with the first guide face and the fourth abutting portion abuts with the fourth guide face and to a second position at which the second abutting portion abuts with the second guide face and the third abutting portion abuts with the third guide face.

* * * * *